(12) United States Patent
Dhillo et al.

(10) Patent No.: US 10,052,317 B2
(45) Date of Patent: Aug. 21, 2018

(54) METHOD FOR TREATING OR PREVENTING HOT FLUSHES

(71) Applicant: Imperial Innovations Limited, Greater London (GB)

(72) Inventors: Waljit Dhillo, Greater London (GB); Channa Jayasena, Greater London (GB)

(73) Assignee: Imperial Innovations Limited, Greater London (GB)

(*) Notice: Subject to any disclaimer, the term of this patent is extended or adjusted under 35 U.S.C. 154(b) by 0 days.

(21) Appl. No.: 14/915,758

(22) PCT Filed: Sep. 5, 2014

(86) PCT No.: PCT/GB2014/052707
§ 371 (c)(1),
(2) Date: Mar. 1, 2016

(87) PCT Pub. No.: WO2015/033163
PCT Pub. Date: Mar. 12, 2015

(65) Prior Publication Data
US 2016/0220555 A1 Aug. 4, 2016

(30) Foreign Application Priority Data
Sep. 5, 2013 (GB) .................................. 1315846.4

(51) Int. Cl.
*A61K 31/47* (2006.01)
*A61K 45/06* (2006.01)
*A61K 31/4545* (2006.01)

(52) U.S. Cl.
CPC .......... *A61K 31/47* (2013.01); *A61K 31/4545* (2013.01); *A61K 45/06* (2013.01)

(58) Field of Classification Search
None
See application file for complete search history.

(56) References Cited

U.S. PATENT DOCUMENTS

| 8,071,621 | B2 * | 12/2011 | Simpson | C07D 215/14 514/313 |
|---|---|---|---|---|
| 2002/0016283 | A1 * | 2/2002 | Guttuso, Jr. | A61K 31/00 514/1 |
| 2003/0092602 | A1 | 5/2003 | Leach et al. | |
| 2005/0163777 | A1 | 7/2005 | Rosen et al. | |
| 2013/0023530 | A1 | 1/2013 | Hoveyda et al. | |
| 2013/0096161 | A1 | 4/2013 | Sun et al. | |

FOREIGN PATENT DOCUMENTS

| WO | 0043008 A1 | 7/2000 |
|---|---|---|
| WO | 0195904 A1 | 12/2001 |
| WO | 03037334 A1 | 5/2003 |
| WO | 2009049791 A2 | 4/2009 |
| WO | 2009062318 A1 | 5/2009 |
| WO | 2010132487 A1 | 11/2010 |
| WO | 2011029099 A1 | 3/2011 |
| WO | 2013050424 A1 | 4/2013 |
| WO | 2014089019 A1 | 6/2014 |

OTHER PUBLICATIONS https://www.rxlist.com/hot_flashes/page4.htm. (Year: 2017).*
https://web.archive.org/web/20130906182957/https://www.prevention.com/mind-body/natural-remedies/natural-menopause-solution-hot-flash-remedies. (Year: 2013).*
Tran, Science, 2009, 324 (5928), 787-790 (Year: 2009).*
Freeman, Menopause (New York, N.Y.). 12(3):258-66, May 2005 (Year: 2005).*
https://web.archive.org/web/20100107140037/http://www.medicinenet.com/hot_flashes/page2.htm#hormone (Year: 2010).*
Search Report issued in corresponding United Kingdom Patent Application No. GB1315846.4 dated Feb. 24, 2014 (5 pages).
International Search Report and Written Opinion issued in corresponding International Patent Application No. PCT/GB2014/052707 dated Dec. 5, 2014 (13 pages).
Albert et al., "Neurokinin-3 receptor antagonists in schizophrenia," Expert Opinion on Therapeutic Patents, 2006, 16(7), pp. 925-937.
AstraZeneca, "AZD2624," Extract from http://openinnovation.astrazeneca.com/what-we-offer/compound/azd2624/ downloaded on Sep. 3, 2014, (1 page).
Dacks et al., "Activation of Neurokinin 3 Receptors in the Median Preoptic Nucleus Decreases Core Temperature in the Rat," Endocrinology, 2011, 152(12), pp. 4894-4905.
Elmore et al., "Synthesis of the NK3 receptor antagonist AZD2624 in C-14-, H-3- and C-13-labeled forms," Journal of Labelled Compounds and Radiopharmaceuticals, 2011, vol. 54, pp. 239-246.
Goodman et al., "Kisspeptin Neurons from Mice to Men: Similarities and Differences," Endocrinology, 2012, 153(11), pp. 5105-5118 (21 pages).
Griebel et al., "Is there still a future for neurokinin 3 receptor antagonists as potential drugs for the treatment of psychiatric diseases?," Pharmacology & Therapeutics, 2012, vol. 133, pp. 116-123.
Malherbe et al., "Tachykinin neurokinin 3 receptor antagonists: a patent review (2005-2010)," Expert Opinion on Therapeutic Patents, 2011, 21(5), pp. 637-655.
Mittelman-Smith et al., "Role for kisspeptin/neurokinin Bldynorphin (KNDy) neurons in cutaneous vasodilatation and the estrogen modulation of body temperature," PNAS, 2012, vol. 109, No. 28, pp. 19846-19851.

(Continued)

*Primary Examiner* — Satyanarayana R Gudibande
(74) *Attorney, Agent, or Firm* — Kilyk & Bowersox, P.L.L.C.

(57) ABSTRACT

The invention provides a neurokinin 3 receptor (NKR3) antagonist for use in the treatment, prevention or amelioration of hot flushes in a human subject, for example a menopausal woman or a patient undergoing cancer therapy which affects secretion of sex steroids. The invention also provides a NKR3 antagonist together with a further active agent, and a composition and a kit comprising a NKR3 antagonist and a further active agent. The invention further provides a NKR3 agonist or exogenous NKB for the induction of hot flushes in a human subject.

13 Claims, 7 Drawing Sheets

(56) References Cited

OTHER PUBLICATIONS

Nakamura et al., "A thermosensory pathway mediating heat-defense responses," PNAS, 2010, vol. 107, No. 19, pp. 8848-8853.
Rance et al., "Modulation of body temperature and LH secretion by hypothalamic KNDy (kisspeptin, neurokinin B and dynorphin) neurons: A novel hypothesis on the mechanism of hot flushes," Frontiers in Neuroendocrinology, 2013, vol. 34, pp. 211-227.
Raini et al., "Rational design of novel pyrrolidine derivatives as orally active neurokinin-3 receptor antagonists," Bioorganic & Medicinal Chemistry Letters, 2010, vol. 20, pp. 6735-6738.
Simonsen et al., "Novel NK3 recptor antagonists for the treatment of schizophrenia and other CNS indications," Current Opinion in Drug Discovery & Development, 2010, vol. 13(4), pp. 379-388.
Spooren et al., "NK3 receptor antagonists: the next generation of antipsychotics?," Nature Reviews Drug Discovery, 2005, vol. 4, pp. 967-975.
Yoshida et al., "Parallel Preoptic Pathways for Thermoregulation," The Journal of Neuroscience, 2009, 29(38), pp. 11954-11964.

\* cited by examiner

Figure 4

| Participant Number | Pre-Study Stress Score (1-3) | Participant-reported symptoms | | Maximum symptoms severity (0-3) |
|---|---|---|---|---|
| | | 1st infusion | 2nd infusion | |
| | | Vehicle | NKB | |
| 1 | 1 | None | Hot forehead, Hot ears, Headache, Warm | 2 |
| 2 | 1 | None | Hot face, Facial flushing, Headache, Warm | 3 |
| 5 | 2 | None | Hot face, 'Hot air blowing on face', Headache, Warm | 2 |
| 7 | 1 | None | None | 0 |
| 9 | 1 | None | Flushing, Clammy, 'Face burning', Warm face/arms | 2 |
| | | NKB | Vehicle | |
| 3 | 2 | Cheeks flushing, Warm | None | 2 |
| 4 | 1 | Warm face, Cold following warm | None | 2 |
| 8 | 1 | None | None | 0 |
| 6 | 1 | Hot head, Sweating, Head tingling, Clammy, Warm | None | 1 |
| 10 | 1 | Feels hot, Face sweating, Warm | None | 1 |

Figure 6 (cont)
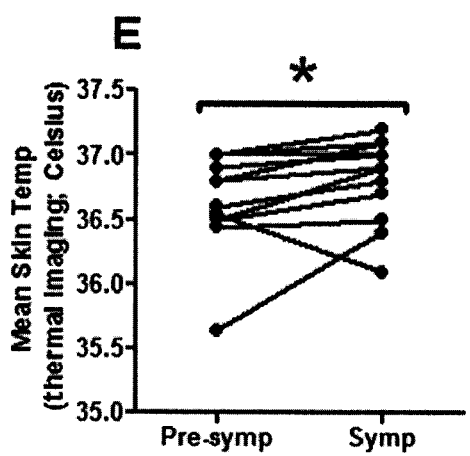
E
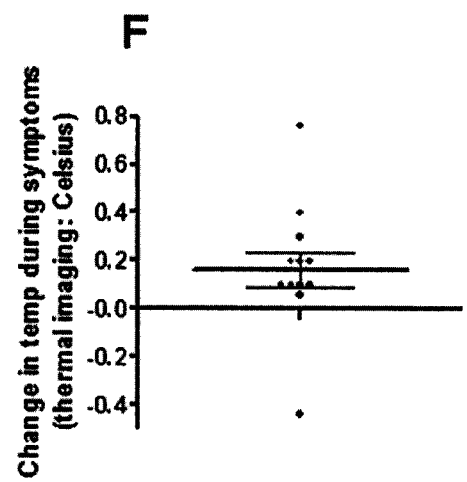
F
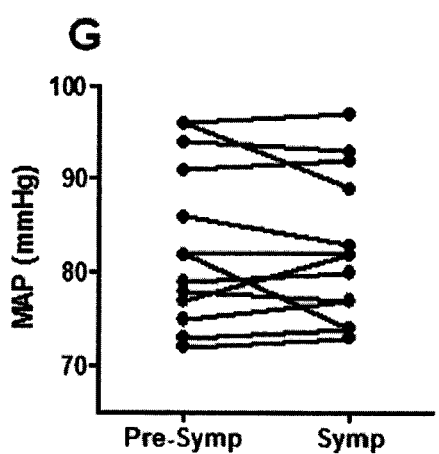
G
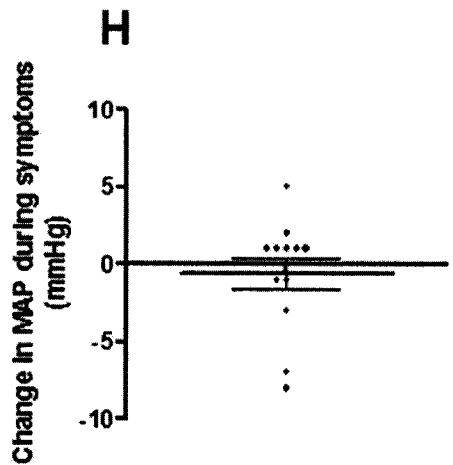
H

METHOD FOR TREATING OR PREVENTING HOT FLUSHES

This application is a National Stage Application of PCT/GB2014/052707, filed Sep. 5, 2014, which claims priority to United Kingdom Patent Application No. 1315846.4, filed Sep. 5, 2013, which is incorporated in its entirety by reference herein.

1. FIELD OF THE INVENTION

This application relates to the use of neurokinin 3 receptor (NKR3) antagonists in the treatment, prevention or amelioration of hot flushes in a human subject, particularly in a subject with of hormonal variation, deficiency or imbalance due to menopause or due to a cancer therapy which affects secretion of sex steroids.

2. BACKGROUND OF THE INVENTION

Hot flushes (or hot flashes or night sweats) are intermittent episodes of sweating and heat sensation associated with deficient circulating sex steroid levels. Hot flushes are experienced by 70-80% of all menopausal women, so affect millions of postmenopausal women worldwide each year, and they can negatively impact on quality of life (Carpenter, J. S., et al. Oncol. Nurs. Forum. 2002. 29(3):16-25; Hunter M., et al. Climacteric. 2010. 14(1):146-151; Archer D. F., et al. Climacteric. 2011. 14(5):515-528; and Thornton J. G., BMJ. 2012. 344). Hot flushes are also experienced by many patients undergoing treatment for cancer, for example patients receiving a breast or prostate cancer treatment which inhibits secretion of oestrogen or testosterone, respectively. Hot flushes induced by medical treatment can be referred to as "iatrogenic hot flushes". Hot flushes are a common and important problem.

Hot flushes arise secondary to deficient circulating sex steroid levels. The exact cause of hot flushes is not well understood.

There are several known treatments for hot flushes. However, current treatments are not completely effective and may confer increased risk of serious complications. Hormone replacement therapy can alleviate hot flushes, but can lead to an increased risk of breast cancer, blood clots and pulmonary embolism (Ruddy K J, Partridge A H. J Clin Oncol. 2012. 30(30): 3705-3711). Selective serotonin reuptake inhibitors (SSRIs), serotonin and norepinephrine reuptake inhibitors (SNRIs), gabapentin and clonidine may also be used for the treatment of hot flushes, but are not always effective at treating symptoms. Hot flushing is without adequate treatment options in clinical practice and therefore represents a substantial health burden without satisfactory therapeutic options.

Neurokinin B (NKB) is a member of the tachykinin family of peptides, which share a common C-terminal amino acid motif (Phe-X-Gly-Leu-Met-NH$_2$) (Maggio J. E. et al. Annu Rev Neurosci 1988. 11:13-28). The other members of the tachykinin family of peptides are substance P and neurokinin A. There are three known tachykinin receptors: neurokinin-1 receptor (NKR1), neurokinin-2 receptor (NKR2) and neurokinin-3 receptor (NKR3). In humans, NKB is encoded by the TAC3 gene and binds preferentially to the neurokinin 3 receptor (Page N. M., Peptides. 2005 26(8): 1356-1368). Substance P and neurokinin A bind preferentially to the neurokinin 1 receptor and neurokinin 2 receptor, respectively.

WO 2003/037334 (Merck & Co. Inc.) describes the use of neurokinin-1 receptor antagonists for the treatment of hot flushes. The treatments described therein have not, as far as the current inventors are aware, been progressed in the clinic. It has been found by Mittelman-Smith M. A., et al that in rats with ovariectomy (surgical removal of the ovaries), ablation of NKB neurones using NK3-saporin prevented an increase in tail skin temperature and decrease in core body temperature, suggesting that NKB-expressing neurons are involved in vasoactive changes observed in ovariectomised rodents (Mittelman-Smith M. A., et al. Proc Natl Acad Sci USA. 2012. 27/109(48): 19846-51). Nakamura et al. and Yoshida et al have reported that the hypothalamic median preoptic nucleus MnPO, which receives information from warm-sensitive, cutaneous thermoreceptors and projects to CNS centres to modulate heat dissipation effectors, is a tissue that expresses the neurokinin 3 receptor (Nakamura K., et al Proc Natl Acad Sci USA. 2010. 107(19): 8848-8853; Yoshida K., et al. J Neurosci. 2009. 29(38):11954-11964). It has been found that C-fos expression (a marker of neuronal activation) in the MnPO is increased in ovariectomised rats when compared with ovariectomised and oestrogen-replaced rats. It was also reported that pharmacological activation of the MnPO by a selective NK3R agonist (senktide) reduced core temperature in ovariectomised rats (Dacks P. A., et al. Endocrinology 2011. 152(12):4894-4905). However, there remains considerable uncertainty about the role of NKR3 in human subjects, and its relevance as a target for treating human diseases.

3. SUMMARY OF THE INVENTION

The invention provides a NK3R antagonist for use in the treatment, prevention or amelioration of hot flushes in a human subject. For example, the subject may be a menopausal woman or a patient undergoing cancer treatment.

The present invention is based on the surprising finding by the inventors that intravenous infusion of NKB induced hot flush-like episodes in healthy, pre-menopausal women and in healthy men.

The invention also provides a method for reducing treating, preventing or ameliorating hot flushes in a subject comprising administering to the subject a NKR3 antagonist.

The invention also provides the use of a NKR3 antagonist for the manufacture of a medicament for treating, preventing or ameliorating hot flushes in a human subject.

4. BRIEF DESCRIPTION OF THE DRAWINGS

FIG. 4 shows the verbal report by participants of any symptoms, including their frequency and severity (0 no symptom, 1 mild heat sensation, 2 strong heat sensation and able to continue with general activity, 3 strong heat sensation unable to continue with current activity), to the study investigators in real-time during a double-blinded administration study of vehicle and neurokinin B; also shown are pre-study stress scores (1 low, 2 medium, 3 high) report by participants that were recorded on arrival for the study.

Figure 5:
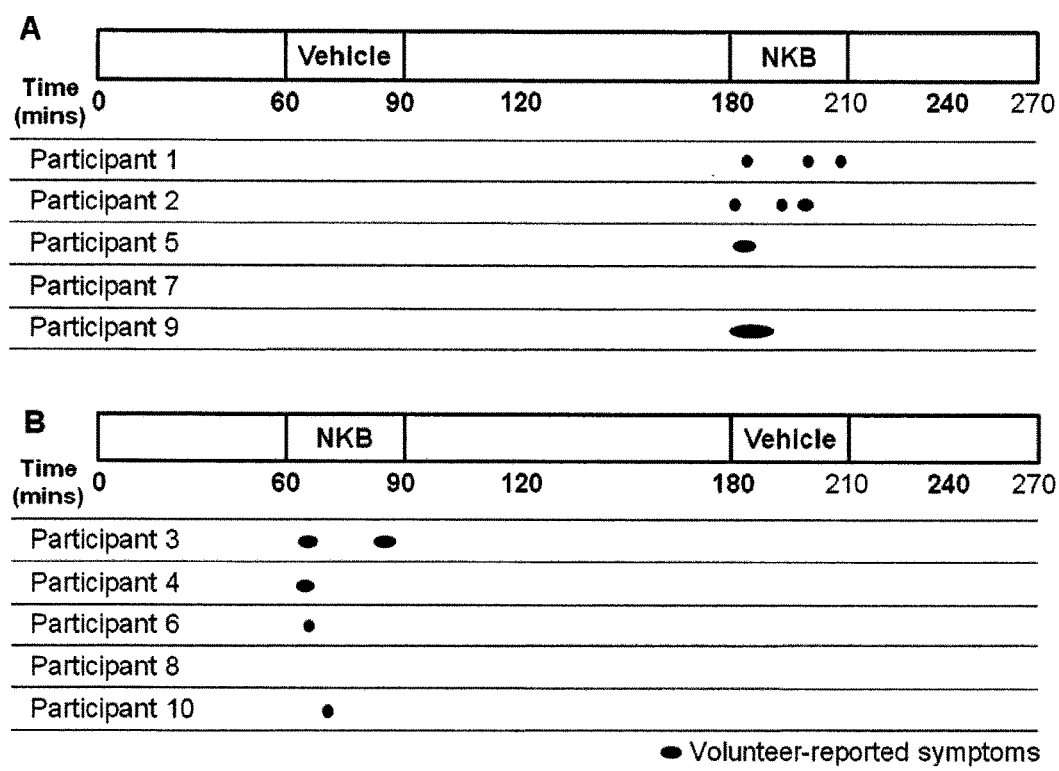

FIG. 5 shows timings and duration (ovals) of participant-reported hot flush symptoms during a double-blinded administration of vehicle and neurokinin B: (A) Participants 1, 2, 5, 7 and 9 received vehicle infusion first and NKB infusion second; (B) Participants 3, 4, 6, 8 and 10 received NKB infusion first then vehicle infusion second.

Figure 6:
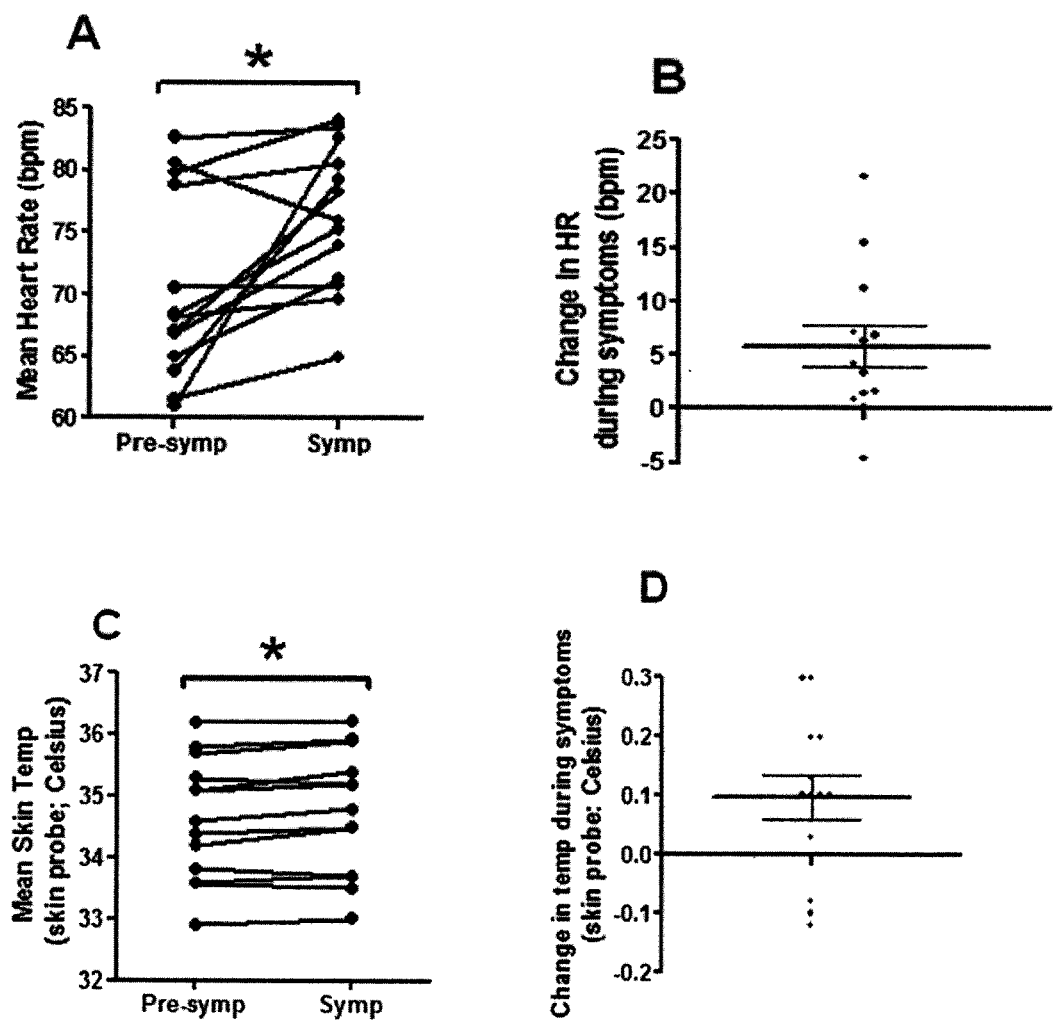

FIG. 6 shows physiological changes (mean heart rate (A), skin temperature by skin probe (C), skin temperature by thermal imaging (E) and mean arterial pressure (MAP) (G)) associated with hot flush episodes in healthy women during 5 minute period pre-symptom onset (Pre-symp) and during symptom period (Symp) using the minutely recordings. FIGS. 5 (B), (D), (F) and (H) show the change in respective physiological parameter when compared with pre-symptom level.

Figure 7:
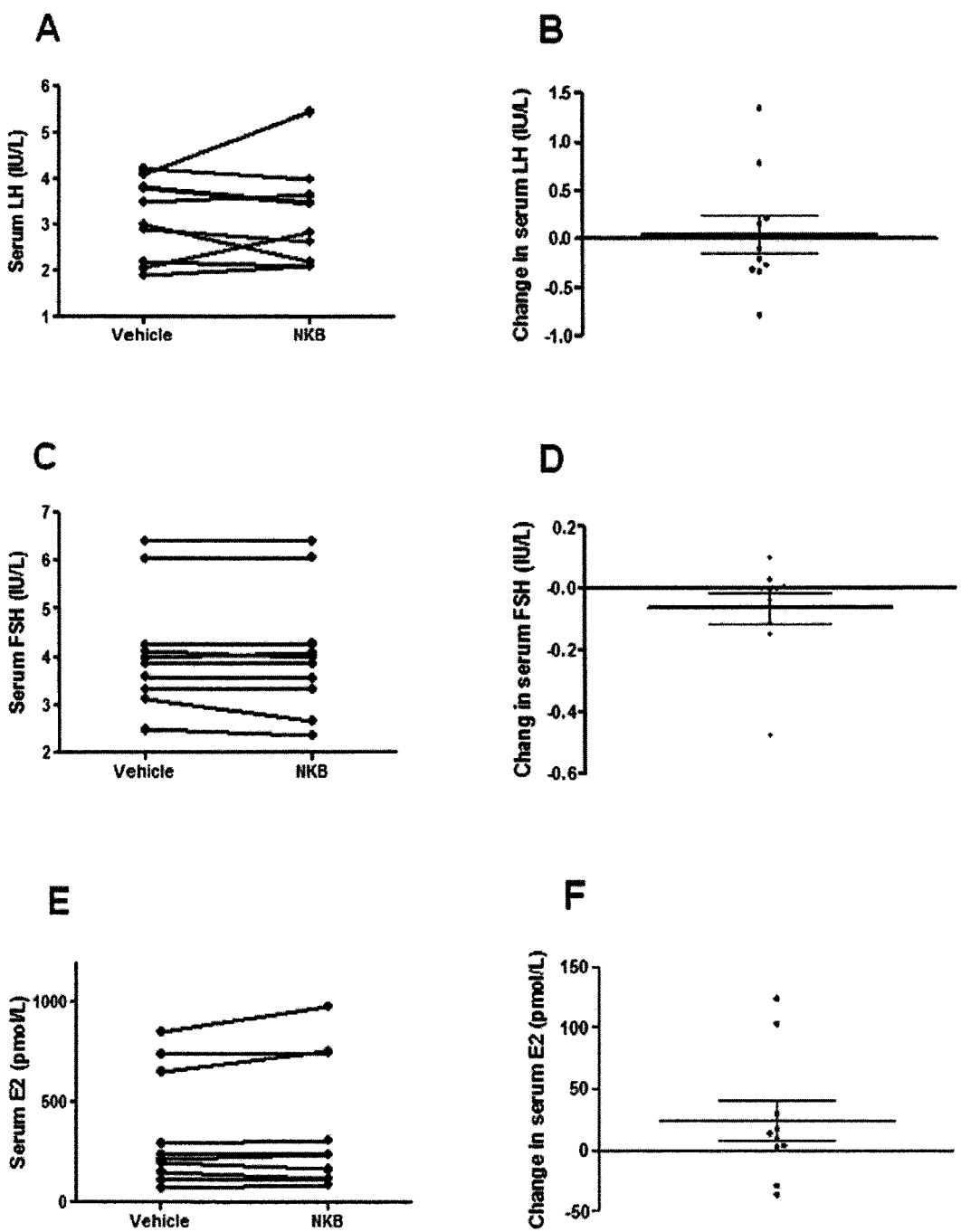

FIG. 7 shows reproductive hormone changes (serum luteinizing hormone (LH) (A), serum follicle stimulating hormone (FSH) (C) and serum estradiol (E)) during neurokinin B and vehicle infusion. FIGS. 6 (B), (D) and (F) show the change in respective parameter when compared with vehicle.

5. DETAILED DESCRIPTION

As described above, the invention relates to the use of a NKR3 antagonist for the treatment, prevention or amelioration of hot flushes in a human subject.

A hot flush includes symptoms such as vasomotor symptoms (i. e. associated with changes in blood flow) that may include sweating on the face, neck and chest and typically manifest during periods of low levels of estrogen in the patient's body. Hormonal changes may be naturally induced (for example by the menopause), drug-induced (for example by antiestrogen or anti-androgen therapy) or surgically induced (for example by oopherectomy or orchiectomy). In particular, the subject is one in need of a treatment, prevention or amelioration of hot flushes, for example a woman experiencing hot flushes as part of the menopause or a subject experiencing hot flushes as a side effect of cancer treatment that affects the hormones of the subject.

The present inventors have studied the effect of intravenous NKB administration on reproductive hormone secretion, and found that intravenous administration of NKB did not stimulate significant reproductive hormone secretion in healthy men. Surprisingly however, the inventors observed that during infusion of the high doses of NKB in male subjects, they complained of hot flush symptoms (heat sensation and flushing).

In further studies, the present inventors found that intravenous administration of NKB did not significantly change reproductive hormone secretion in healthy women without deficient oestrogen levels. The present inventors found that exogenous NKB induces hot flush episodes in the same healthy female volunteers.

Menopausal flushing is known to be associated with increases in heart rate and skin temperature (Carpenter J S, et al, Oncology Nursing Forum (2002) 29:E16-E25). During menopausal hot flushes, heart rate (HR) has been reported to increase by approximately 5-15 beats per minute without coincident change in blood pressure (Casper R F, Yen S S, Clin Endocrinol (1985) 22:293-312), and increases in skin temperature of 0.2-1.0° C. have also been reported (Molnar G W, J, Appl. Physiol. (1975) 38:499-503; Sturdee D W, Reece B L, Maturitas (1979) 1:201-205). The present inventors have also found that intravenous administration of NKB in healthy women without deficient oestrogen levels lead to elevations in heart rate (beats per minute) and skin temperature (measured using skin probe and thermal imaging camera) during hot flush episodes, and by similar magnitudes during flushing episodes, when compared with pre-symptom levels. No flushing symptoms were recorded in the same volunteers during vehicle infusions. Thus intravenous infusion of NKB acutely induces hot flushes in women.

Further, overall mean levels of HR, mean arterial blood pressure (MAP) and skin temperature were similar between NKB and vehicle infusions in healthy women, which suggests that NKB per se does not affect these parameters: changes were specific and confined to hot flush episodes. These results further suggest that NKB elicits hot flushing episodes in women, which are accompanied by objective physiological effects. Effects of NKB on reproductive hormone release was also measured by the present inventors (Example 4) and found to have no significant effects on reproductive hormone release at the NKB dose tested.

It is known that levels of endogenous NKB are elevated during conditions of sex steroid deficiency (such as during the menopause) in women. The present inventors have now found that exogenous NKB induces hot flushes analogous to those observed during menopause in healthy women with normal menstrual cycles, and in healthy men.

As exogenous NKB has now been shown to recapitulate the effects of hot flushes during the human menopause, this provides for the first time evidence that physiological mechanisms behind hot flushes in humans are related to NKB signaling. These results have notable therapeutic implications: pharmacological blockade of NKB signaling is expected to provide a means to treat, prevent or ameliorate hot flushes in humans. As NKR3 is the endogenous receptor for NKB, pharmacological blockade of NKB signaling is achieved by a NKR3 antagonist.

Conditions and Subjects:

The invention provides the use of a NKR3 antagonist for the treatment, prevention or amelioration of hot flushes in a human subject. Typically, the subject is a menopausal female and/or a subject undergoing cancer treatment. Where the subject is undergoing cancer treatment, that cancer treatment can be a treatment which affects the hormonal levels of the subject, for example, hormonal therapy treatment for breast cancer, ovarian cancer and prostate cancer. Examples of hormonal therapies for cancers include: selective estrogen receptor antagonists including tamoxifen (NOLVADEX®), raloxifene (EVISTA®), lasofoxifene (FABLYN) and toremifene (FARESTON®); antiestrogen drugs including fulvestrant (FASLODEX®); aromatase inhibitors including anastrozole (ARIMIDEX®), letrozole (FEMARA®), vorozole (RIVIZOR), formestane (LENTARON), fadrozole (AFEMA) and exemestane (AROMASIN®); luteinizing-hormone-releasing hormone (LHRH) agonists including goserelin (ZOLADEX®), leuprolide (LUPRON®); luteinising hormone (LH) blockers including buserelin, leuprorelin (PROSTAP®), histrelin (VANTAS®), deslorelin (SU-PRELORIN), nafarelin (SYNAREL) and triptorelin (DECAPEPTYL®); anti androgens including flutamide (DROGENIL®), nilutamide (NILANDRON(USA)/ANANDRON (Canada)) and bicalutamide (CASODEX®); gonadotrophin releasing hormone (GnRH) blocker including degarelix (FIRMAGON®); and Abiraterone (ZYTIGA®).

The subject may also have undergone ovarian ablation, for example surgically in an operation to remove the ovaries or by treatment with radiation.

More preferably the subject is a woman, and even more preferably the subject is an elderly woman, or a woman who is menopausal or otherwise suffering from hormonal variations, hormonal deficiency or symptoms of hormonal changes which result in hot flushes. The subject may have hormonal variations that are naturally induced, induced by treatment or therapy, or surgically-induced. Examples of naturally induced hormonal variations are: menopause, perimenopause, climacteric menopause and premature menopause. Examples of treatment or therapy induced hormonal variation are listed above as the examples of hormonal therapies for cancers, including chemotherapy and radiation of the pelvis. Examples of surgically-induced hormonal variations are hysterectomy, oopherectomy, orchiectomy, or any other process that impairs ovarian blood supply.

NKR3 Antagonists

A NKR3 antagonist is a compound capable of binding to neurokinin 3 receptor sites and blocking the actions of a neurokinin 3 receptor agonist, for example neurokinin B.

NKR3 antagonists are known in the art. NKR3 antagonists have been shown to potentially be useful in the treatment of schizophrenia and drug addiction. Work is continuing to develop further NKR3 antagonists. Some of the known NKR3 antagonists are listed in Malherbe, P., et al, Expert Opin. Ther. Patents. 2011. 21:637-655 and Griebel, G., et al. Pharmacology & Therapeutics. 2012. 133: 116-123.

A NKR3 antagonist for use in the invention preferably has an inhibitory activity $IC_{50}$ of less than 100 µM. For example it may have a level of inhibition of NKR3 in the range of $IC_{50}$ 0.001 to 99.9 µM. Preferred NKR3 antagonists are those which exhibit inhibitory activity at lower concentrations within that $IC_{50}$ range. For example, in the range of 0.001 to 5 µM, or 0.001 to 0.1 µM.

Certain NKR3 antagonist compounds have NKR3 binding activity in the range of $pK_i$ of greater than 4, for example 4 to 10. Preferred NKR3 antagonists of the invention are those which have NKR3 binding activity at higher values within the $pK_i$ range shown above. For example, in the range of 5.5 to 10, or 7 to 10.

Preferably the NKR3 antagonist is selective for NKR3 over NKR1 and NKR2. By "selective NKR3 antagonist" is meant a NKR3 antagonist of with an $IC_{50}$ value for NKR3 which is lower than the $IC_{50}$ value for each of NKR1 and NKR2, for example lower by a factor of 3 times, more preferably 10 times, more preferably 100 times and still more preferably 1000 times. Preferably NKR3 antagonists of the invention have $pK_i$ values for NKR3 which are greater than the $pK_i$ values for each of NKR1 and NKR2 by more than 0.25, preferably greater by more than 0.5, more preferably greater by more than 1 and even more preferably greater by more than 1.5 units.

A neurokinin 3 receptor antagonist may be a peptidyl or a non-peptidyl compound. In a preferred embodiment a NKR3 antagonist for use in the invention is a non-peptidyl compound. Certain NKR3 antagonists have been known for many years and they have been under development for the treatment of psychiatric disorders, in particular schizophrenia. Three NKR3 antagonists have undergone Phase II clinical trials. Those are Osanetant ((R)-N-{{3-[1-Benzoyl-3-(3,4-dichlorophenyl)piperidin-3-yl]prop-1-yl}-4-phenylpiperidin-4-yl}-N-methylacetamine) (I), Talnetant (3-hydroxy-2-phenyl-N-(1-phenylpropyl)quinoline-4-carboxamide) (II) and the compound AZD2624 (3-(hydrosulfonylamino)-2-phenyl-N-[(1S)-1-phenylpropyl]quinoline-4-carboxamide) (III). Osanetant, Talnetant and AZD2624 are selective for NKR3 over NKR1 and NKR2 (Spooren, W., et al. Nature Reviews Drug Discovery. 2006. ISSN 1474-1776; Griebel, G., et al. Pharmacology & Therapeutics. 2012. 133: 116-123; Elmore, C. S., et al, J. Label Compd. Radiopharm. 2011. 54: 239-246).

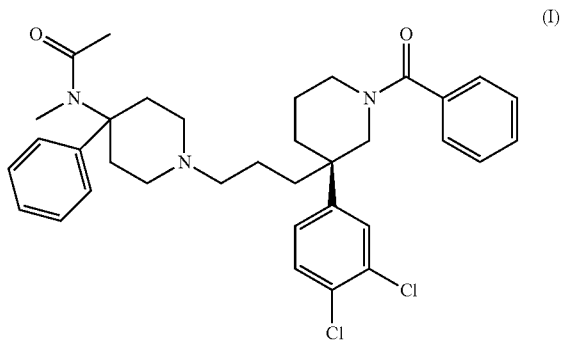

(I)

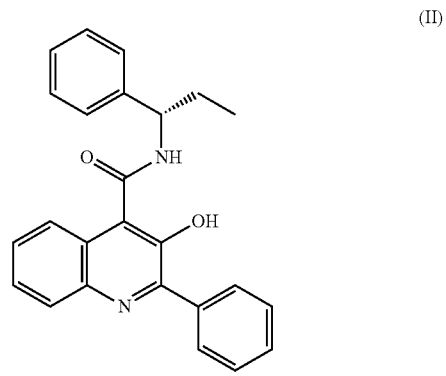

(II)

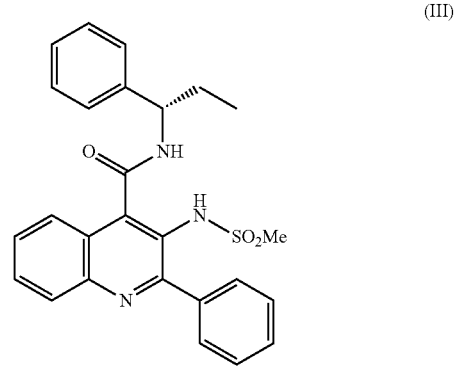

(III)

Other known selective NKR3 antagonists are SB 222200 ((S)-3-Methyl-2-phenyl-N-(1-phenylpropyl)-4-quinolinecarboxamide) (IV), SB 218795 ((−)-(R)-N-(α-Methoxycarbonylbenzyl)-2-phenylquinoline-4-carboxamide) (V) and SSR 146977 hydrochloride (N1-[1-3-[(3R)-1-Benzoyl-3-(3,4-dichlorophenyl)-3-piperidinyl]propyl]-4-phenyl-piperidinyl]N,N-dimethylurea hydrochloride) (VI).

(IV)
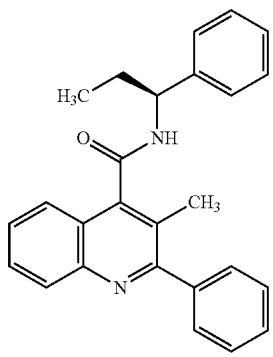
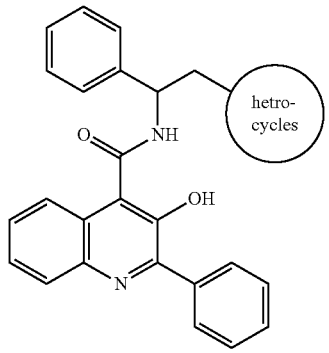
(V)
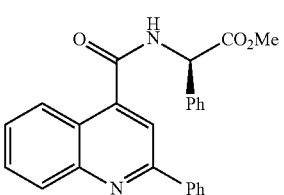
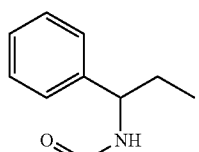
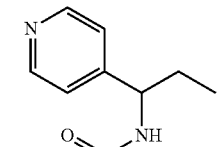
(VI)
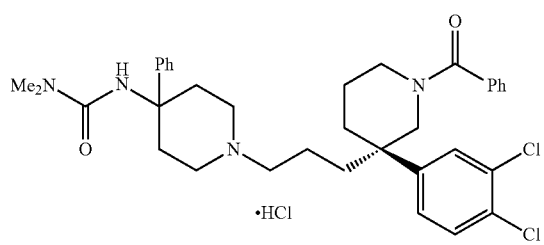
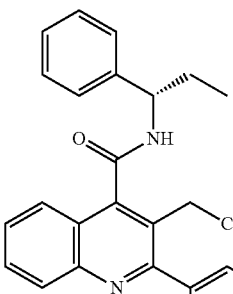
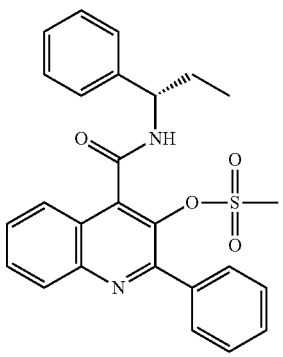
In one preferred embodiment the NKR3 antagonist is selected from the group consisting of Osanetant, Talnetant, AZD2624, SB222200, SB 218795 and SSR 146977 hydrochloride. More preferably it is selected from the group consisting of SB222200, SB 218795 and AZD2624. Most preferably it is AZD2624.
Certain other NKR3 antagonists have the following structures:
Group A:
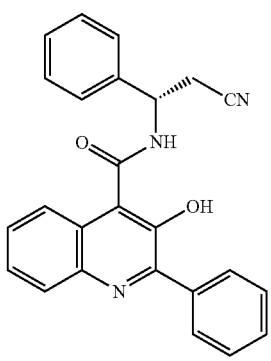
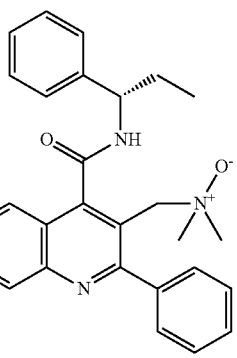
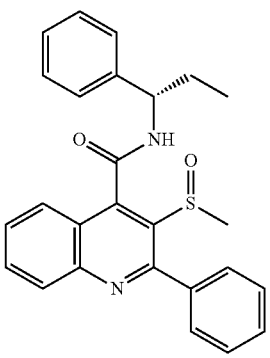

-continued
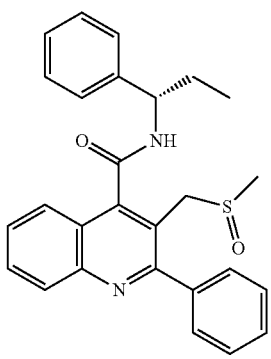 [SMILES: CC[C@H](NC(=O)c1c(CS(C)=O)c(-c2ccccc2)nc2ccccc12)c1ccccc1]
Group B:
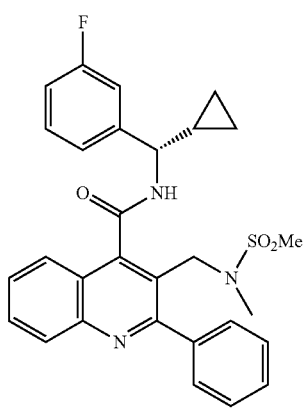
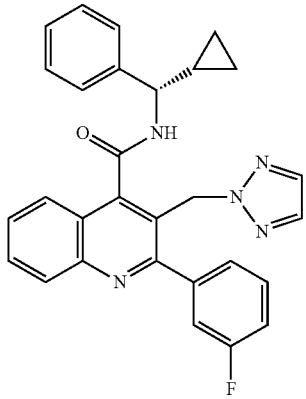
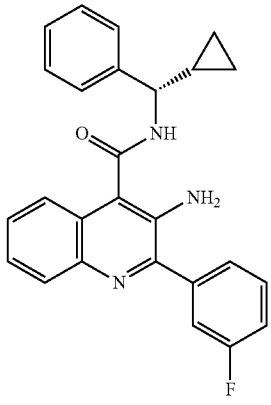
Group C:
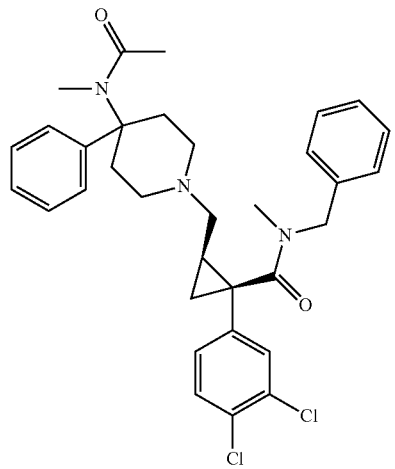
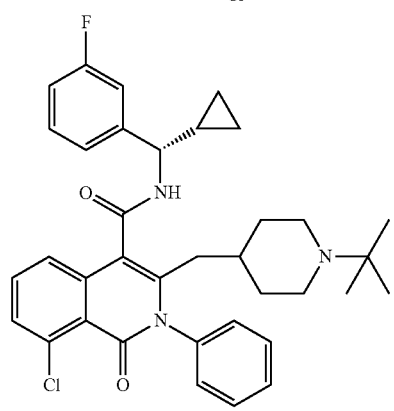
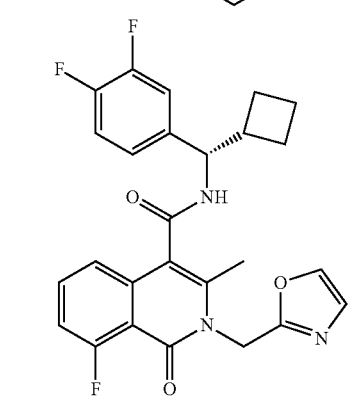
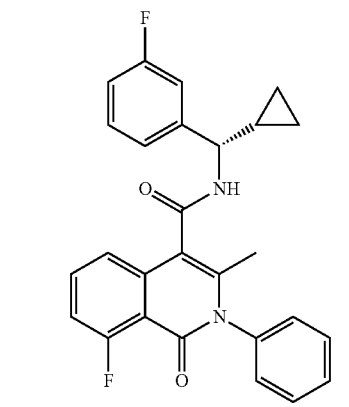

-continued
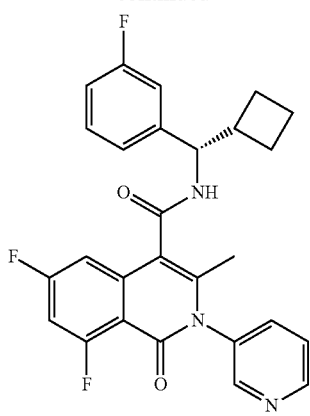
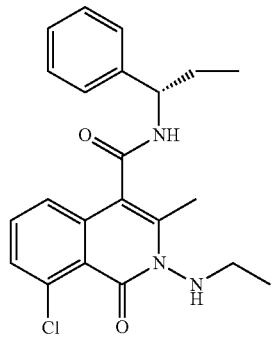
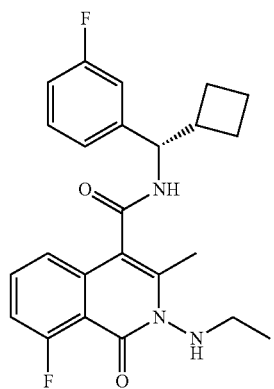
Group D:
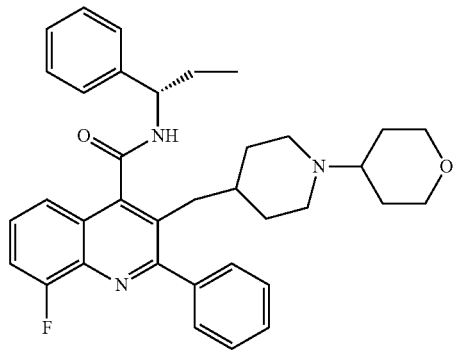
-continued
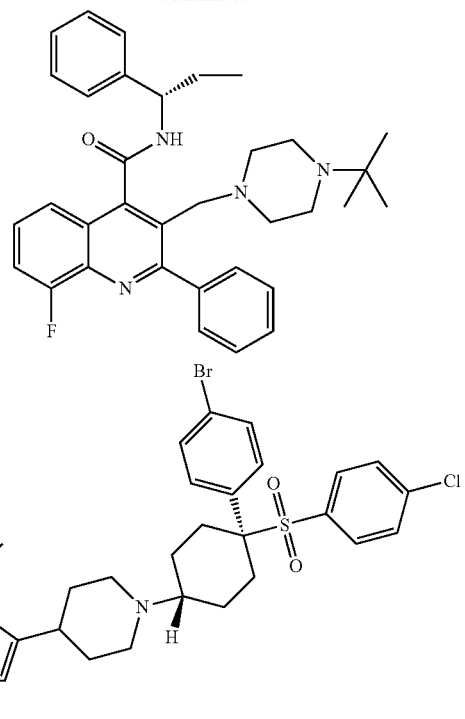
Group E:
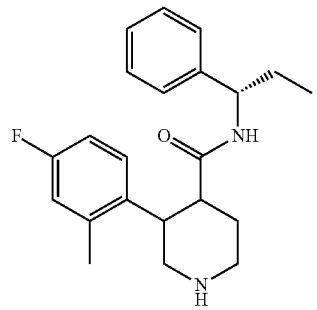 [SMILES: CC[C@H](NC(=O)C1CCNCC1c1ccc(F)cc1C)c1ccccc1]
Group F:
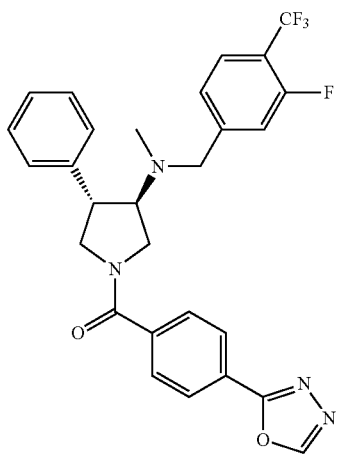

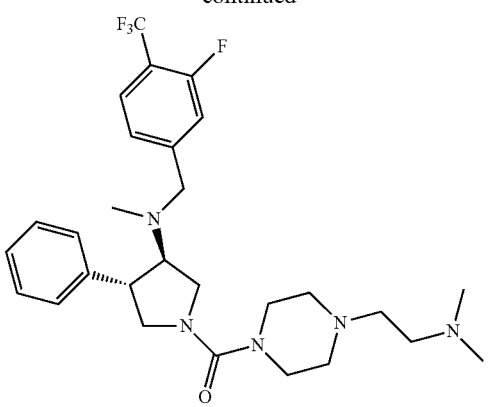

Group G:

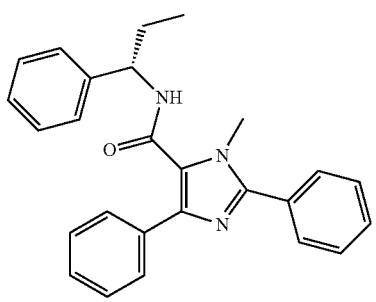

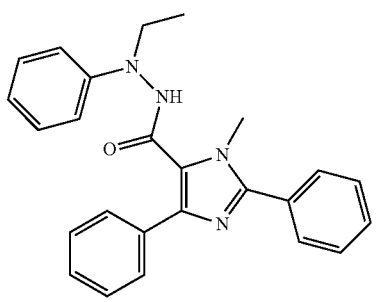

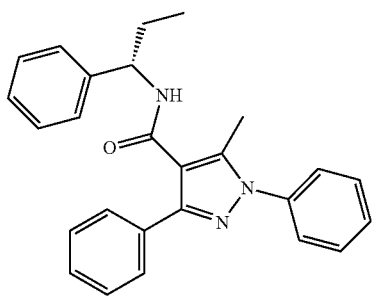

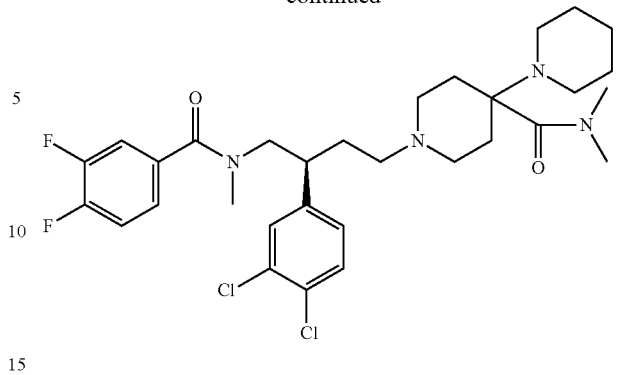

Further details regarding the compounds of Groups A to G can be found in Malherbe, P., et al, Expert Opin. Ther. Patents. 2011. 21: 637-655 and the documents cited therein.

Further NKR3 antagonists are described in the following documents and the documents cited therein: Malherbe, P., et al, Expert Opin. Ther. Patents. 2011. 21: 637-655; Griebel, G., et al. Pharmacology & Therapeutics. 2012. 133: 116-123; Spooren, W., et al. Nature Reviews Drug Discovery. 2006. ISSN 1474-1776; Simonsen K. B., et al, Curr Opin Drug Discov Devel. 2010. 13(4): 379-88; Ratni, et al, Bioorg & Med Chem Letters. 2010. 20: 6735-38; and Albert, S. A., et al, Expert Opinion on Therapeutic Patents. 2006. 16(7): 925-937; US 2013-0096161 (N30 Pharmaceuticals, Inc).

Antagonism of NKR3 can be achieved by antibodies and antibody fragments that specifically bind to neurokinin B and inhibit the activity of neurokinin B. NKB is the natural ligand for the NKR3. An anti-NKB antibody or fragment thereof diminishes or abolishes the ability of neurokinin B to bind to NK3R and consequently can affect NKB signaling in the same manner as the small molecule NKR3 antagonists mentioned above. Therefore, a NKR3 antagonist for use in the current invention may be an antibody or antibody fragment that specifically binds to neurokinin B and inhibits the activity of neurokinin B or a fragment thereof. Anti-NKB antibodies or fragments thereof are described in, for example, US 2005/0163777.

Depending upon the substituents present in the NKR3 antagonist for use in the present invention, the compounds may form esters, amides, carbamates and/or salts. Salts of compounds of the invention which are suitable for use in medicine are those wherein a counterion is pharmaceutically acceptable. However, salts having non-pharmaceutically acceptable counterions are within the scope of the present invention, for example, for use as intermediates in the preparation of the compounds of the invention and their pharmaceutically acceptable salts, and physiologically functional derivatives. By the term "physiologically functional derivative" is meant a chemical derivative of a compound of the invention having the same physiological function as the free compound of the invention, for example, by being convertible in the body thereto. Esters, amides and carbamates are examples of physiologically functional derivatives.

Suitable salts of the NKR3 antagonist for use in the present invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

A compound which, upon administration to the recipient, is capable of being converted into a compound of the invention as described above, or an active metabolite or residue thereof, is known as a "prodrug". A prodrug may, for example, be converted within the body, e. g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference. The NKR3 antagonist for use in the present invention may have an appropriate group converted to an ester, an amide or a carbamate.

Those skilled in the art of organic chemistry will appreciate that many organic compounds can form complexes with solvents in which they are reacted or from which they are precipitated or crystallized. These complexes are known as "solvates".

Dosages:

The amount of NKR3 antagonist to be administered to a subject is preferably a therapeutically effective amount. A "therapeutically effective amount" in the context of the NKR3 antagonist for use in the current invention is an amount sufficient to treat, prevent or ameliorate hot flushes in a subject. The amount of active ingredient (the NKR3 antagonist) which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. Typically, a daily dose will be in the range of 0.001 mg per kg of body weight per day (mg/kg/day) to 100 mg/kg/day, for example 0.01 to 20 mg/kg/day, for example 0.05 to 10 mg/kg/day, for example 0.05 to 1 mg/kg/day. An ordinarily skilled physician, veterinarian or clinician can readily determine and prescribe the effective amount of the drug required to prevent, counter or arrest the progress of the condition.

Preferably, the NKR3 antagonist is administered orally, intravenously or transdermally. Oral dosages of NKR3 antagonist for use in the present invention will range between about 0.01 mg/kg/day to about 100 mg/kg/day, preferably from 0.01 to 10 mg/kg/day, and most preferably from 0.1 to 5.0 mg/kg/day. For oral administration, the compositions are preferably provided in the form of tablets or other forms of presentation provided in discrete units. For example, they may contain 0.01, 0.05, 0.1, 0.5, 1.0, 2.5, 5.0, 7.5, 10.0, 15.0, 20.0, 25.0, 50.0, 100 or 500 milligrams of the active ingredient NKR3 antagonist, preferably, for example, they may contain 2.5, 5.0, 7.5 or 10.0 milligrams of the active ingredient NKR3 antagonist. They may be administered in a single daily dose, or the total daily dosage may be administered in divided doses of two, three or four times daily.

For example, the NKR3 antagonist may be administered orally in a dose of from 1 to 1500 mg per day, for example from 10 to 1200 mg per day. In one embodiment the NKR3 antagonist may be administered orally in a dose of from 10 to 100 mg per day, for example from 20 to 80 mg per day (for example 20, 40, 60 or 80 mg), for example from 20 to 60 mg per day. Those dosages are particularly suitable for AZD2624. In another embodiments, the NKR3 antagonist may be administered orally in a dose of from 25 to 1200 mg per day (for example 25, 100, 200, 400, 600, 800, 1000 or 1200 mg), for example from 100 to 800 mg per day. Those dosages are particularly suitable for Talnetant or Osanetant.

For intravenous administration, the most preferred doses will range from about 0.005 mg/kg/day to about 80 mg/kg/day, preferably from 0.005 to 5 mg/kg/day, and most preferably from 0.05 to 3.0 mg/kg/day. The preferred infusion rate will range from 0.1 to about 10 mg/kg/minute during a constant rate infusion. An NKR3 antagonist can be administered by a transdermal route, for example using a transdermal skin patch. Daily dose from a patch will range from about 0.001 mg/kg/day to about 10 mg/kg/day, preferably from 0.001 to 5 mg/kg/day, and most preferably from 0.01 to 2.0 mg/kg/day. An NKR3 antagonist can be administered using a reservoir device. A reservoir device is device which is implanted under the skin and allows slow release of a drug over a period of time, for example months or years. For example, the drug may dispersed in a polymer which is implanted under the skin to allow for controlled, slow release of the drug into the patient. Daily dose from a reservoir device will range from about of 0.001 mg/kg/day to about 10 mg/kg/day, preferably from 0.001 to 3 mg/kg/day, and most preferably from 0.01 to 1.0 mg/kg/day.

Combination Treatments

Whilst a NKR3 antagonist for use in the present invention may be used as the sole active ingredient in a medicament, it is also possible for the NKR3 antagonist to be used in combination with one or more further active agents. Accordingly there is provided a NKR3 antagonist for use in the present invention, together with a further active ingredient. The NKR3 antagonist and further active agent are for simultaneous, sequential or separate administration. The further active ingredient is typically present in a therapeutically effective amount. In embodiments which provide NKR3 antagonist for use in the present invention, together with a further active ingredient, preferably the NKR3 antagonist is selected from the group consisting of Osanetant, Talnetant, AZD2624, SB222200, SB 218795 and SSR 146977 hydrochloride. In one embodiment the NKR3 antagonist is selected from the group consisting of Osanetant, Talnetant and AZD2624; in another embodiment it is selected from the group consisting of SB222200, SB 218795, SSR 146977 hydrochloride and AZD2624. Most preferably it is AZD2624.

Such a further active ingredient may be a further NKR3 antagonist, or it may be a different type of therapeutic agent, for example an agent useful for treatment of other signs or symptoms of hormonal variation, for example an estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRI's), serotonin and norepinephrine reuptake inhibitors (SNRIs), gabapentin, clonidine, tibolone, Hormone Replacement Therapy (HRT), oestrogen-only HRT, high dose progesterogens (for example Medroxyprogesterone Acetate and Megestrol Acetate), natural progesterone cream, 5HT-2 antagonist, non-steroidal anti-inflammatory drug, oral contraceptive, progesterone, progestin, monoamine oxidase inhibitor, carbohydrate mixture and the like, or physical method such as a cooling agent.

In one preferred embodiment, the further active ingredient is estrogen, estrogen receptor modulator, estrogen agonist, selective serotonin reuptake inhibitor (SSRI's), serotonin and norepinephrine reuptake inhibitors (SNRIs), gabapentin, clonidine, tibolone, oestrogen-only Hormone Replacement Therapy (HRT), oestrogen and progesterone HRT, progesterone or progestin.

In one embodiment the further active ingredient is one used in the treatment or symptoms of the menopause, for example Clonidine, Conjugated Oestrogens, Conjugated oestrogens/Medroxyprogesterone acetate, Conjugated Oestrogens/Norgestrel, Drospirenone/Estradiol hemihydrate, Drospirenone/Estradiol Hemihydrate, Dydrogesterone/Estradiol, Estradiol Valerate/Norethisterone, Estradiol, Estradiol hemihydrate, Estradiol/Estriol/Estrone, estradiol hemihydrate, Estradiol/Levonorgestrel, Estradiol/Norethisterone, Estradiol/Norethisterone acetate, Estradiol Valerate, Estradiol valerate/Medroxyprogesterone acetate, Estradiol valerate/Norgestrel, Estropipate, Ethinylestradiol, Ortho-Gynest, Ovestin, Progesterone, and Tibolone.

In one embodiment the further active ingredient may be, for example an agent useful for treatment of other signs or symptoms of hormonal variation, for example an estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRI's), 5HT-2 antagonist, non-steroidal anti-inflammatory drug, oral contraceptive, progesterone, progestin, monoamine oxidase inhibitor, carbohydrate mixture and the like, or physical method such as a cooling agent.

Further examples of compounds that the present invention may be taken in combination with include estrogen, progesterone, clonidine, venlafaxine, megestrol acetate, mirtazapine, a non-steroidal antiinflammatory, such as acetomeniphen, alprostadil, asprin, diclofenac, etodolac, ibuprofen, indomethacin, ketoprofe, ketorolac tromethamine, misoprostol, nabumetone, naproxen, naproxen sodium, oxaprozin, piroxicam, spironolactone, spironolactone with hydrochlorothiazide, or trovafloxacin; a corticosteroid; a selective cyclooxygenase-2 inhibitor, such as celecoxib, etoricoxib, parecoxib, rofecoxib, valdecoxib, meloxicam, flosulide, nimesulide, MK-663, NS 398, DuP 697, SC-58125, SC-58635, or RS 57067; adinazolam, abiraterone, allobarbital, alonimid, alprazolam, amitriptyline, amobarbital, amoxapine, anastrozole, bentazepam, benzoctamine, bicalutamide, brotizolam, bupropion, buserelin, busprione, butabarbital, butalbital, capuride, carbocloral, chloral betaine, chloral hydrate, chlordiazepoxide, clomethrone, clomipramine, cloperidone, clorazepate, clorethate, clozapine, cyprazepam, degarelix, delmadinone, desipramine, deslorelin, dexclamol, diazepam, dichloralphenazone, divalproex, diphenhydramine, doxepin, droloxifene, estazolam, estradiol, estrogen, ethchlorvynol, etomidate, exemestane, fadrozole, fenobam, flunitrazepam, flurazepam, flutamide, fluvoxamine, fluoxetine, formestane, fosazepam, fulvestrant, glutethimide, goserelin, halazepam, histrelin, hydroxyzine, idoxifene, imipramine, lasofoxifene, leuprolide, lithium, letrozol, leucine, leuprolide, leuprorelin, lorazepam, lormetazepam, maprotiline, mecloqualone, melatonin, mephobarbital, meprobamate, methaqualone, midaflur, midazolam, nafarelin, nafoxidine, nefazodone, nitromifene, nilutamide, nisobamate, nitrazepam, nociceptin, nortriptyline, ormeloxifene, oxazepam, paraldehyde, paroxetine, pentobarbital, perlapine, perphenazine, phenelzine, phenobarbital, prazepam, progesterone, promethazine, propofol, protriptyline, quazepam, raloxifene, reclazepam, roletamide, secobarbital, sertraline, suproclone, tamoxifene, temazepam, thioridazine, toremifene, tracazolate, tranylcypromaine, trazodone, trioxifene, triazolam, triptorelin, trepipam, tricetamide, triclofos, trifluoperazine, trimetozine, trimipramine, uldazepam, valproate, venlafaxine, vorozole, zaleplon, zolazepam, zolpidem, and salts thereof, and combinations thereof, and the like, as well as admixtures and combinations thereof.

Further examples of compounds that the present invention may be taken in combination with include: selective estrogen receptor antagonists including tamoxifen (NOLVADEX®), raloxifene (EVISTA®), and toremifene (FARESTON®); antiestrogen drugs including fulvestrant (FASLODEX®); aromatase inhibitors including anastrozole (ARIMIDEX®), letrozole (FEMARA®) and exemestane (AROMASIN®); Luteinizing-hormone-releasing hormone (LHRH) agonists including goserelin (ZOLADEX®), leuprolide (LUPRON®); Luteinising hormone (LH) blockers including buserelin, leuprorelin (PROSTAP®), histrelin (VANTAS®) and triptorelin (DECAPEPTYL®); Anti androgens including flutamide (DROGENIL®) and bicalutamide (CASODEX®); Gonadotrophin releasing hormone (GnRH) blocker including degarelix (FIRMAGON®); and Abiraterone (ZYTIGA®). Those are examples of hormonal therapies for cancers.

The above other active agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more further active agent(s), either concurrently or sequentially, the weight ratio to the additional agent is preferably within the range from about 10:1 to about 1:10.

Compositions

While it is possible for the NKR3 antagonist for use in the present invention to be administered alone, it is preferable for it to be present in a pharmaceutical formulation or composition. Accordingly, the invention provides a composition comprising a NKR3 antagonist for use in the treatment, prevention or amelioration of hot flushes in a human subject. Such a composition may further comprise a pharmaceutically acceptable diluent, excipient or carrier (collectively referred to herein as "carrier" materials).

The invention also provides a composition comprising:
a NKR3 antagonist, and
a further active agent,
for example a further active agent selected from the group consisting of an estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRI's), serotonin and norepinephrine reuptake inhibitors (SNRIs), gabapentin, clonidine, tibolone, Hormone Replacement Therapy (HRT), oestrogen-only HRT, high dose progesterogens (for example Medroxyprogesterone Acetate and Megestrol Acetate), natural progesterone cream, 5HT-2 antagonist, non-steroidal anti-inflammatory drug, oral contraceptive, progesterone, progestin, monoamine oxidase inhibitor, carbohydrate mixture and the like, and a physical method such as a cooling agent. The composition finds use as a medicament, for example in the treatment, prevention or amelioration of hot flushes in a human subject.

In one embodiment the further active agent is selected from estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRI's), 5HT-2 antagonist, non-steroidal anti-inflammatory drug, oral contraceptive, progesterone, progestin and monoamine oxidase inhibitor.

The pharmaceutical formulations for use in the present invention include those suitable for oral, parenteral (including subcutaneous, intradermal, intramuscular, intravenous [bolus or infusion], and intraarticular), inhalation (including fine particle dusts or mists which may be generated by means of various types of metered does pressurized aerosols, nebulizers or insufflators) rectal, intraperitoneal or topical (including dermal, buccal, sublingual, and intraocular) administration.

The preferred pharmaceutical formulations for use in the present invention are those suitable for oral, intravenous or transdermal administration.

Formulations for use in the present invention which are suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

The NK3R antagonist for use in the present invention can also be administered in a liposome delivery system, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain a preservatives (for example a benzyl alcohol), an absorption promoter to enhance bioavailability, and/or a solubilizing or dispersing agent.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations for use in the present invention may include other agents conventional in the art having regard to the type of formulation in question, for example those suitable for oral administration may include flavouring agents.

The invention also provides a kit comprising:
a NKR3 antagonist, and
a further active agent,
for example a further active agent selected from the group consisting of an estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRPs), serotonin and norepinephrine reuptake inhibitors (SNRIs), gabapentin, clonidine, tibolone, Hormone Replacement Therapy (HRT), oestrogen-only HRT, high dose progesterogens (for example Medroxyprogesterone Acetate and Megestrol Acetate), natural progesterone cream, 5HT-2 antagonist, non-steroidal anti-inflammatory drug, oral contraceptive, progesterone, progestin, monoamine oxidase inhibitor, carbohydrate mixture and the like, and physical method such as a cooling agent, the NKR3 antagonist and further active agent being for co-administration simultaneously, separately or sequentially.

In one embodiment, the further active agent is selected from estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRI's), 5HT-2 antagonist, non-steroidal anti-inflammatory drug, oral contraceptive, progesterone, progestin, monoamine oxidase inhibitor and a physical cooling agent.

The present also invention provides the use of exogenous NKB or a NKR3 agonist for the induction of hot flushes in a human subject. Induction of hot flushes may have, for example, utility for studying the physiological effects of a hot flush in a human subject. It may also have utility for in vivo testing of efficacy of compounds in humans which may be of use for the treatment of hot flushes.

EXAMPLES

The invention is illustrated by the following non-limiting Examples.

Example 1

Observations in Dose-Finding Study with Intravenous Infusion of NKB to Healthy Men Neurokinin B Human sequence neurokinin B was synthesised by Bachem Holding AG (Bubendorf, Switzerland), and purified by reverse-phase high performance liquid chromatography (HPLC). Electrospray mass spectroscopy and amino acid analysis confirmed identity of the peptide (lot:3007511). The Limulus amoebocyte lysate test detected no endotoxin (Associates of Cape Cod, Liverpool, UK), and bacterial culture was sterile (Department of Microbiology, Hammersmith Hospital, London, UK) in samples of neurokinin B peptide. Vials of freeze-dried neurokinin B were stored at −20° C. and reconstituted in 0.9% saline.

Subjects 23 healthy male subjects participated in the study (mean age of 23 subjects: 29.0±1.3 years; mean body mass index of 23 subjects: 23.3±0.3 kg/$m_2$), following ethical approval (reference:10/H0707/68) and written consent, in accordance with The Declaration of Helsinki. No subjects had any history of hot flushes, deficient levels of sex hormones, or were receiving any regular medications.

Protocol

Studies were performed in the Clinical Investigation Unit, during which subjects asked to lay supine. This study was blinded to subjects but not investigators. NKB was dissolved in a vehicle consisting of saline containing Gelofusin (5% vol/vol) (B. Braun Medical, Sheffield, UK) to minimize peptide adsorption. The infusion rate of peptide was halved 30 min after commencing infusion in order to achieve a steady-state concentration of peptide administration during the infusion period. Continuous cardiac monitoring was performed during all studies, and two experienced physicians were in attendance at all times. Heart rate, blood pressure, and adverse symptoms were recorded at regular intervals.

Each volunteer received 90-min IV infusion of vehicle or NKB (initial rate 0.04, 0.16, 0.64, 2.56, 5.12, or 10.24 nmol/kg/h) (n=4-5/dose). A cannula was inserted into a large forearm vein in both arms: one for collection of blood, and the second for NKB infusion. Blood was sampled at −20, −10 and 0 min, immediately after which the infusion was started. Blood was then sampled at 15, 30, 45, 60, 75, 90, 120, 150, 180, 210 and 240 min. Blood samples were collected for measurement of serum luteinising hormone (LH), follicle stimulating hormone (FSH), and testosterone at all time points.

Results

No adverse effects were observed during an initial dose-finding study of 90 min intravenous infusion of NKB (initial rate 0.04 to 5.12 nmol/kg/h) in healthy male subjects. However, in 2 of 3 subjects given a higher dose of NKB (10.24 nmol/kg/h) administration resulted in mild vasomotor symptoms, including hot flushing, sinus tachycardia and hypertension. After the administration was discontinued the symptoms resolved fully within 5 minutes.

Example 2

Intravenous Infusion of NKB to Healthy Women

Material and Methods

Study Subjects

Eight healthy female subjects participated in the study, following ethical approval (reference: 10/H0707/68) and written consent, in accordance with The Declaration of Helsinki. All subjects had regular periods. No subjects had any history of hot flushes, deficient levels of sex hormones, or were receiving any regular medications.

Neurokinin B

Human sequence neurokinin B was obtained and used as described above.

Protocol

Each volunteer received 180-min IV infusion of saline placebo or NKB (initial rate 0.04, 0.16, 0.64, 2.56, 5.12, or 10.24 nmol/kg/h) (n=5-7/dose). Continuous cardiac monitoring was performed. Heart rate, blood pressure, and adverse symptoms were recorded at regular intervals. Participants were asked to complete a symptom diary in order to measure subjective frequency and problem rating of hot flushes during each study visit. All subjects also completed a questionnaire at the end of each study visit to summarise the symptoms that they experienced that day. Data was analysed by an investigator in a blinded manner.

Data Analysis

Data are presented as mean±standard error of mean (SEM). Multiple means were compared using one-way ANOVA with Dunnett's post-hoc test. Pairs of means were compared using paired two-tailed t-tests.

Results

Figure 1:
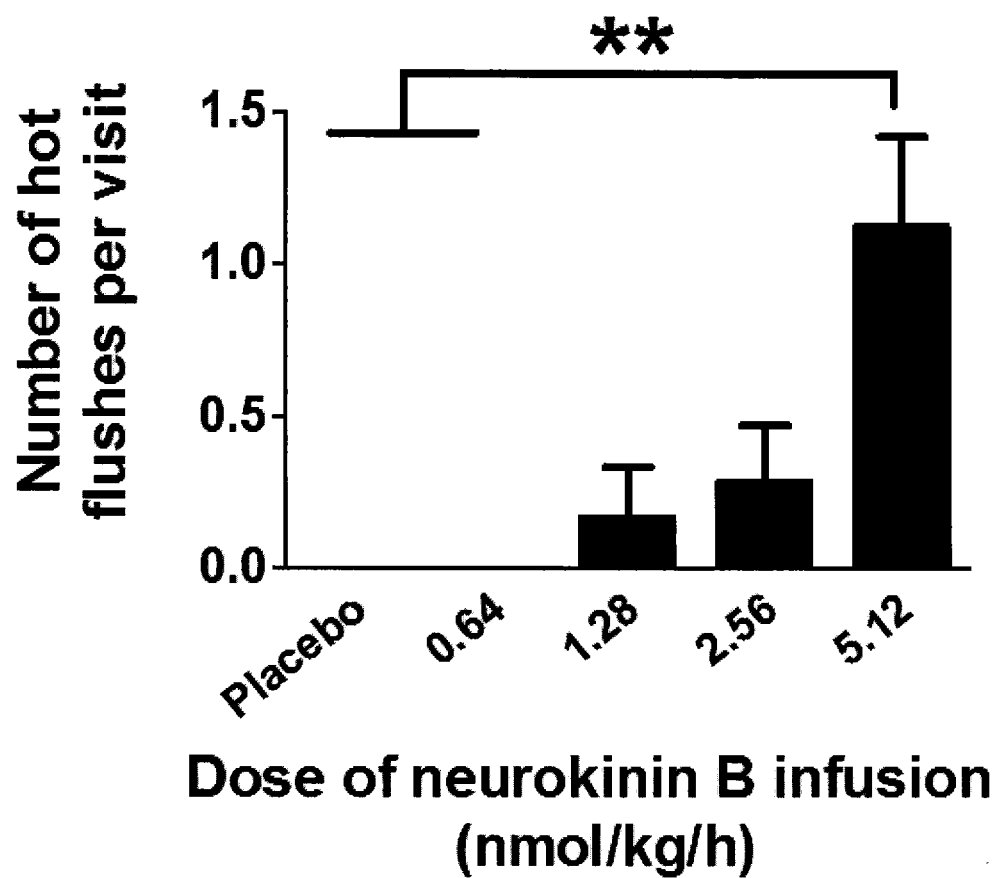
FIG. 1 shows the number of hot flushes experienced by healthy, pre-menopausal women when given a placebo or an increasing dose of intravenous NKB.

No hot flushes were experienced by any healthy women during infusion of saline placebo or the lowest dose of NKB (0.64 nmol/kg/h) (FIG. 1). However 7/8 healthy women experienced hot flushes during infusion of the highest dose of NKB (5.12 nmol/kg/h) (mean number of hot flushes per visit: placebo: 0; NKB 5.12 nmol/kg/h: 1.13±0.30, P<0.01 vs. placebo). Hot flushes were also experienced by 2/7 healthy women during infusion of 2.56 nmol/kg/h NKB, and by 1/6 women during infusion of 1.28 nmol/kg/h NKB. These results are shown in FIG. 1. Data shown in FIG. 1 are mean±SEM. P<0.01 vs. placebo.

Example 3

Symptom Assessment Study During Intravenous (iv) Infusion of NKB to Healthy Women Material and Methods
Study Subjects Five healthy female volunteers participated in the study (mean age 37.8±1.7y; mean body mass index 21.9±0.7 kg/m2), following ethical approval (reference: 10/H0707/68) and written consent, in accordance with The Declaration of Helsinki. Participants had no medical problems, were not on any regular medication and had regular menstrual cycles. Participants attended in the mornings and during the follicular phase of their menstrual cycle to minimise physiological changes in body temperature occurring during sleep and associated with ovulation (1) (Day of menstrual cycle: 8.0±0.9)

Neurokinin B

Human sequence neurokinin B was obtained and used as described above.

Protocol

Figure 2:
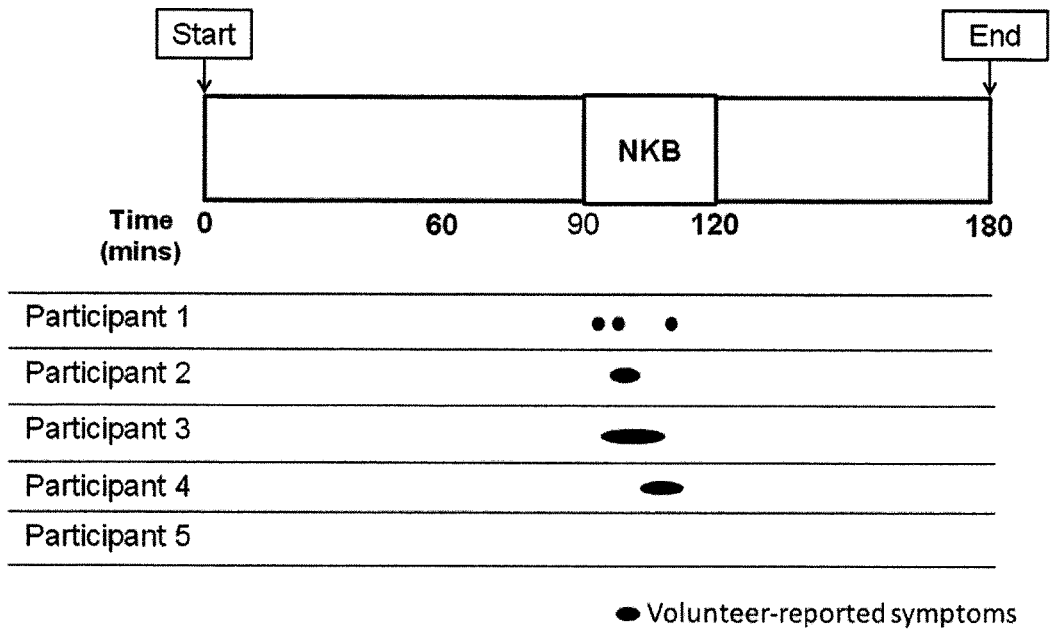
FIG. 2 shows the timings and duration of participant-reported hot flush symptoms (ovals) during 30 minute intravenous infusion of neurokinin B.

Participants were admitted in the morning to the Clinical Investigation Unit between days 3 and 10 of their menstrual cycle, and asked to lay supine for the 180 minute study duration (FIG. 2). A cannula was inserted into a large forearm vein and NKB (5.12 nmol/kg/min) was administered by intravenous (iv) infusion for 30 min commencing at t=90 min. This dose of NKB was selected as it was the maximal dose that was well-tolerated dose experiment 1, above. NKB was dissolved in saline containing gelofusin (5% vol/vol) (B. Braun Medical, Sheffield, UK) to minimize peptide adsorption (Kraegen E W, Lazarus L, Meler H, Campbell L, Chia Y O, Br Med J (1974), 3:464-466). Participants (but not investigators) were blinded as to the identity of the infusion (NKB or vehicle, however all participants received NKB). Participants were informed before the study that they may experience body sensations or symptoms and they were asked to report these in real time during the study. Participants were not specifically informed that they may experience 'hot flush' symptoms so as to minimise reporting bias.

Data Analysis

Data are presented as mean±standard error of mean (SEM). Means were compared using two-tailed paired t-tests. $p<0.05$ was considered statistically significant.

Results

Flushing symptoms (e.g. warmth, heat, sweating) were only reported during NKB infusion with no flushing symptoms reported during the 90 minutes pre-NKB infusion or the 60 minutes post-NKB infusion. Flushing was reported by four out of the five participants during NKB infusion (P<0.05 vs. vehicle) (FIG. 2). Three of the four participants experiencing flushing reported a single flushing episode during NKB infusion, and one participant experienced three flushing episodes during NKB infusion.

Example 4

Detailed Physiological Assessment Study During iv Infusion of NKB and Vehicle to Healthy Women Material and Methods
Study Subjects Ten healthy female volunteers participated in the study (mean age 35.3±1.3y; mean body mass index 22.1±0.7 kg/m2), following ethical approval (reference: 10/H0707/68) and written consent, in accordance with The Declaration of Helsinki. Participants had no medical problems, were not on any regular medication and had regular menstrual cycles. Participants attended in the mornings and during the follicular phase of their menstrual cycle to minimise physiological changes in body temperature occurring during sleep and associated with ovulation (1) (Day of menstrual cycle: 5.9±0.6)

Neurokinin B

Human sequence neurokinin B was obtained and used as described above.

Protocol

Figure 3:
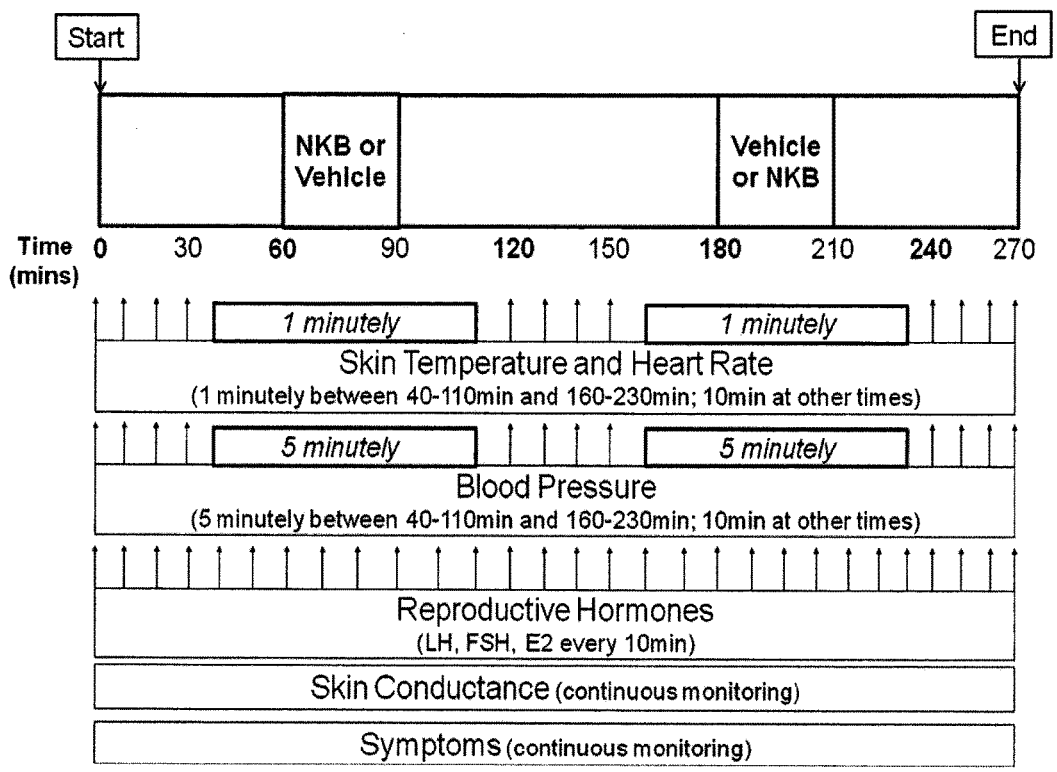
FIG. 3 shows the protocol diagram for a double-blinded administration study of vehicle and neurokinin B.

Having observed in Example 3 that participants reported flushing during NKB infusion, a double-blinded placebo-controlled study was carried out. This was performed in a climate-controlled Clinical Research Unit with ambient temperature 24° C. and humidity 50% as has been established in previous studies to be a suitable environment to investigate menopausal flushing (e.g. de Bakker I P, Everaerd W, Maturitas (1996) 25:87-98; Carpenter J S, Gilchrist J M, Chen K, Gautam S, Freedman R R, Menopause: The Journal of The North American Menopause Society (2004) 11:375-381). Participants were admitted on a morning between days 3 and 10 of their menstrual cycle, and asked to lay supine for the 270 minute study duration (FIG. 3). A cannula was inserted into a large forearm vein in both arms: one for collection of blood, and the second for vehicle (gelofusin) or NKB infusion. 30 minute iv infusion of either NKB (5.12 nmol/kg/h) or vehicle (equivalent volume) were commenced at t=60 min and t=180 min, by an investigator blinded to the identity of each infusion. Each participant received one NKB infusion and one vehicle infusion, randomised and prepared by an independent investigator. Participants were informed that they could receive any of the following: NKB followed by vehicle; vehicle followed by NKB; NKB twice; vehicle twice. This strategy ensured integrity of blinding, since any symptoms experienced during the first infusion would not allow participants to automatically deduce the identity of the second infusion.

In order to prevent confounding factors which may affect flushing, participants were asked to refrain from hot drinks, caffeine, alcohol and spicy foods for 12 hours preceding the study start and for the duration of the study. All participants wore light cotton standard hospital gowns. All studies commenced between 9.30-10.30 am. Two experienced physicians were in attendance at all times. Symptoms, heart rate, blood pressure, sweating and skin temperature monitoring were performed as detailed below:

Heart Rate (HR) and Mean Arterial Blood Pressure (MAP): HR was recorded minutely for 20 minutes pre-infusion until 20 minutes post-infusion. MAP was recorded at 5 minute intervals (to minimize discomfort) for 20 minutes pre-infusion until 20 minutes post-infusion. At other times HR and MAP were recorded at 10 minute intervals (FIG. 3). MAP (in mmHg) was calculated using the following standard formula: MAP=((2×diastolic BP)+systolic BP)/3.

Skin Temperature: Skin temperature was recorded each minute for 20 minutes pre-infusion until 20 minutes post-infusion and at 10 minute intervals at other times. Skin temperature was measured by skin temperature probe attached to the neck (Mindray, Huntingdon, UK) and by thermal imaging camera (T440Bx, Flir, Wilsonville, USA). Thermal imaging temperature values were determined by in-built software which recorded the highest temperature point in a box constructed to contain the shoulders and head of the participant.

Skin Conductance: Increased skin conductance is an objective marker of sweating which occurs in menopausal flushing. Sternal skin conductance (SSC) was measured using a previously described Bahr hot flush monitor that measured SSC in microsiemens (μS) every 10 seconds by passing an electric current across two electrodes attached to the sternal region of the chest (Simplex Scientific, Wisconsin, USA) (Mann E, Hunter M S, Menopause (2011) 18:709-722; Stefanopoulou E, Hunter M S, Am. J. Hum. Biol. (2014) 26:389-394; Bahr D E, et al, Physiol Meas (2014) 35:95-110).

Symptoms: On arrival on the study day participants were asked to report their general stress level that day on a scale 1-3 (1-no stress, 2-mild stress, 3-high stress) (FIG. 4). They were also asked to verbally report any symptoms of any nature that they experienced including their frequency and severity to the study investigators in real-time during the study. Participants were informed before the study that they may experience body sensations or symptoms but were not specifically informed that they may experience 'hot flush' symptoms so as to minimise reporting bias. Symptom data was collected by an independent investigator blinded to the identities of infusions administered during the study.

Reproductive Hormones: Blood was collected for luteinizing hormone (LH), follicle stimulating hormone (FSH) and estradiol (E2) at intervals of 10 minutes throughout the study. Blood samples for serum analysis were collected in plain serum Vacutainer tubes (Beckton Dickson, Franklin Lakes, N.J., USA), and allowed to clot prior to centrifugation and separation. Serum LH, FSH and estradiol were measured using automated chemiluminescent immunoassays (Abbott Laboratories, Abbott Park, Ill., USA). Reference ranges were as follows: LH (follicular), 2-10 IU/L; FSH (follicular), 4-14 IU/L; estradiol (follicular)<1000 pmol/L. The respective intraassay and interassay coefficients of variation were: 4.1 and 2.7% (LH); 4.1 and 3.0% (FSH); 3.6 and 3.4% (estradiol). Conversion factors for estradiol from International Units to Mass Units (pmol/L to pg/mL): x(1/3.67).

Data Analysis

Data are presented as mean±standard error of mean (SEM). Means were compared using two-tailed paired t-tests. $p<0.05$ was considered statistically significant.

Results

Flushing Episodes During Vehicle and NKB: No flushing symptoms were recorded during infusion of vehicle in healthy women (FIG. 5). Flushing symptoms were only reported during NKB infusion and ranged from mild to strong. During NKB infusion eight out of ten participants experienced flushing (of these participants, five experienced a single flushing episode, one experienced two flushing episodes, and two participants each experienced three flushing episodes) (FIG. 5 and FIG. 4). All first flushing episodes commenced between 1-12 minutes after NKB infusion initiation (FIG. 5). Concordant increases in sternal skin conductance (suggestive of sweating) were evident in six of the eight participants at the time of flushing during their NKB infusion (concordance was defined as an objectively-measured sternal skin conductance response corroborated by a subjective self-report of a flush (Mann E, Hunter M S, Menopause (2011) 18:709-722)).

Changes in Heart Rate, Temperature and Blood Pressure During Flushing Episodes: It was investigated specifically whether HR, temperature (measured using skin temperature probe and thermal imaging camera), or MAP were altered specifically during flushing symptoms occurring during NKB infusion. Mean HR increased significantly during flushing symptoms when compared with the pre-symptom period (mean HR in bpm: 70.3±2.1, pre-symptoms; 76.2±1.6, symptoms, $p<0.05$ vs. pre-symptoms) (FIG. 6A-B). Mean skin temperature increased significantly during flushing symptoms when compared with the pre-symptom period, whether measured using skin probe (mean temperature in Celsius: 34.6±0.2, pre-symptoms; 34.7±0.3, symptoms, $p<0.05$ vs. pre-symptoms) or using thermal imaging camera (mean temperature in Celsius: 36.7±0.1, pre-symptoms; 36.8±0.1, symptoms, $p<0.05$ vs. pre-symptoms) (FIG. 6C-F). No significant change in MAP was observed flushing symptoms when compared with the pre-symptom period (mean MAP in mmHg: 83.2±8.6, pre-symptoms; 82.5±2.2, symptoms, p=ns vs. pre-symptoms) (FIG. 6G-H).

Overall Changes in Heart Rate, Temperature and Blood Pressure During Entire Vehicle and NKB Infusions: No overall changes in HR, skin temperature (measured using skin probe or thermal imaging camera), or mean arterial blood pressure (MAP) were observed between vehicle and NKB infusions when comparing the measurements over the entire duration of the infusion; hence physiological changes were specific to hot flush episodes and not present for the duration of NKB infusion.

Changes in Serum Reproductive Hormones During Vehicle and NKB: No significant changes in serum LH, FSH or estradiol were observed during the entire 30 minute NKB infusion period when compared with vehicle infusion period (FIG. 7).

Example 5

Administration of a NKR3 Antagonist to Menopausal Women with Hot Flush Symptoms

Material and Methods
Study Subjects

Female subjects participate in the study, following ethical approval and written consent, in accordance with The Declaration of Helsinki. Subjects have a history of hot flushes and deficient levels of sex hormones.

Protocol

Each subject receives a therapeutically effective dose of a NKR3 antagonist or a placebo. The subjects are monitored for a period of time of between 4 and 24 hours and the frequency and severity of hot flash symptoms are measured, for example by heart rate, blood pressure, body temperature, perspiration, adverse symptom and/or subjective symptom monitoring and recorded at regular intervals and/or if a subject has a hot flush episode. Subjective symptom monitoring can be during and/or after the monitoring period.

Example 5a

Administration of a AZD2624 Antagonist to Menopausal Women with Hot Flush Symptoms Material and Methods
Study Subjects Female subjects participate in the study, following ethical approval and written consent, in accordance with The Declaration of Helsinki. Subjects have a history of hot flushes and deficient levels of sex hormones.

Protocol

Each subject receives a therapeutically effective dose of AZD2624 (for example 20 to 80 mg per day, for example 20, 40, 60 or 80 mg) or a placebo. The subjects are monitored for a period of time of between 4 and 24 hours and the frequency and severity of hot flash symptoms are measured, for example by heart rate, blood pressure, body temperature, perspiration, adverse symptom and/or subjective symptom monitoring and recorded at regular intervals and/or if a subject has a hot flush episode. Subjective symptom monitoring can be during and/or after the monitoring period.

The invention claimed is:

1. A method for reducing, treating or ameliorating hot flushes in a subject in need thereof, comprising administering to the subject a NKR3 antagonist, wherein the NKR3 antagonist is selective for NKR3 over NKR1 and NKR2, and with the proviso that the NKR3 antagonist is not selected from the group consisting of (R)-N-{{3-[1-Benzoyl-3-(3,4-dichlorophenyl)piperidin-3-yl]prop-1-yl}-4-phenylpiperidin-4-yl}-N-methylacetamine and 3-hydroxy-2-phenyl-N-(1-phenylpropyl)quinoline-4-carboxamide.

2. The method of claim 1, wherein the antagonist is selected from the group consisting of (3-((methylsulfonyl)amino)-2-phenyl-N-(1-phenylpropyl)quinoline-4-carboxamide, (S)-3-Methyl-2-phenyl-N-(1-phenylpropyl)-4-quinolinecarboxamide, (−)-(R)-N-(α-Methoxycarbonylbenzyl)-2-phenylquinoline-4-carboxamide and N1-[1-3-[(3R)-1-Benzoyl-3-(3-(3,4-dichlorophenyl)-3-piperidinyl]propyl]-4-phenyl-piperidinyl]-N,N-dimethylurea hydrochloride.

3. The method of claim 1, wherein the compound is administered orally, intravenously or transdermally.

4. The method of claim 1, wherein the subject is a menopausal female.

5. The method of claim 1, wherein the subject is a human undergoing treatment for cancer.

6. The method of claim 1, wherein the NKR3 antagonist is administered in a dose from 1 to 1200 mg per day.

7. The method of claim 1, wherein said NKR3 antagonist is administered together with a further active agent, where the further active agent is selected from the group consisting of an estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRI's), 5HT-2 antagonist, non-steroidal anti-inflammatory drug, oral contraceptive, progesterone, progestin, monoamine oxidase inhibitor and a physical cooling agent.

8. The method of claim 7, wherein the further active agent is: selected from the group consisting of estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRI's), serotonin and norepinephrine reuptake inhibitors (SNRIs), gabapentin,clonidine, tibolone, Hormone Replacement Therapy (HRT), oestrogen-only HRT, high dose progesterogens, natural progesterone cream, 5HT-2 antagonist, non-steroidal anti-inflammatory drug, oral contraceptive, progesterone, progestin, monoamine oxidase inhibitor, carbohydrate mixture, or a cooling agent; or selected from the group consisting of Clonidine, Conjugated Oestrogens, Conjugated oestrogens/Medroxyprogesterone acetate, Conjugated Oestrogens/Norgestrel, Drospirenone/Estradiol hemihydrate, Drospirenone/Estradiol Hemihydrate, Dydrogesterone/Estradiol,Estradiol Valerate/Norethisterone, Estradiol, Estradiol hemihydrate, Estradiol/Estriol/Estrone, estradiol hemihydrate, Estradiol/Levonorgestrel, Estradiol/Norethisterone, Estradiol/Norethisterone acetate, Estradiol Valerate, Estradiol valerate/Medroxyprogesterone acetate, Estradiol valerate/Norgestrel, Estropipate, Ethinylestradiol, Ortho-Gynest, Ovestin, Progesterone, and Tibolone; or selected from the group consisting of tamoxifen, raloxifene, and toremifene; antiestrogen drugs including fulvestrant; aromatase inhibitors including anastrozole, letrozole and exemestane; Luteinizing-hormone-releasing hormone (LHRH) agonists including goserelin, leuprolide; Luteinising hormone (LH) blockers including buserelin, leuprorelin, histrelin and triptorelin; Anti androgens including flutamide and bicalutamide; Gonadotrophin releasing hormone (GnRH) blocker including degarelix; and Abiraterone.

9. The method of claim 1 wherein the NKR3 antagonist is present in a composition.

10. The method of claim 9, wherein said composition comprises:
the NKR3 antagonist, and
a further active agent
selected from the group consisting of an estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRI's), 5HT-2 antagonist, non-steroidal anti-inflammatory drug, oral contraceptive, progesterone, progestin and monoamine oxidase inhibitor.

11. The method of claim 10 wherein the antagonist is selected from the group consisting of 3-((methylsulfonyl)amino)-2-phenyl-N-(1-phenylpropyl)quinoline-4-carboxamide, (S)-3-Methyl-2-phenyl-N-(1-phenylpropyl)-4-quinolinecarboxamide, SB (−)-(R)-N-(α-Methoxycarbonylbenzyl)-2-phenylquinoline-4-carboxamide and N1-[1-3-[(3R)-1-Benzoyl-3-(3-(3,4-dichlorophenyl)-3-piperidinyl]propyl]-4-phenyl-piperidinyl]-N,N-dimethylurea hydrochloride and where the further active agent is selected from the group consisting of an estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbituate, serotonin (5-HT) agonist, selective serotonin reuptake inhibitor (SSRI's), 5HT-2 antagonist, non-steroidal anti-inflammatory drug, oral contraceptive, progesterone, progestin, monoamine oxidase inhibitor and a physical cooling agent.

12. The method of claim 7 wherein the NKR3 antagonist and further active agent are co-administered simultaneously, separately, or sequentially.

13. The method of claim 1, wherein the NKR3 antagonist is selected from the group consisting of

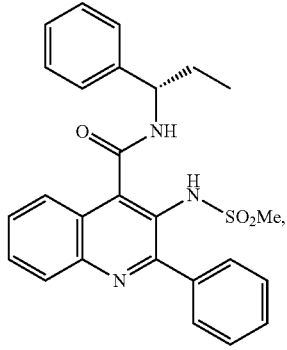

-continued
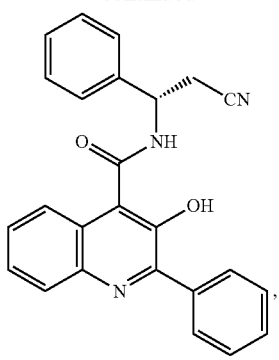
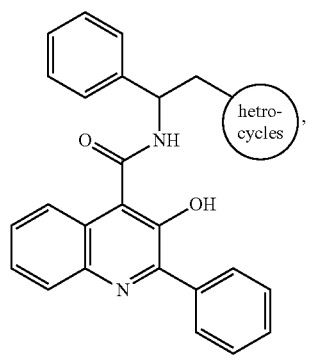
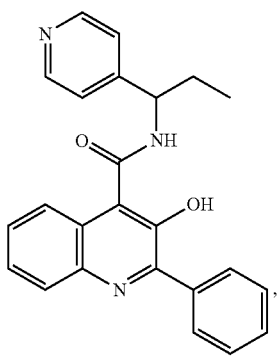
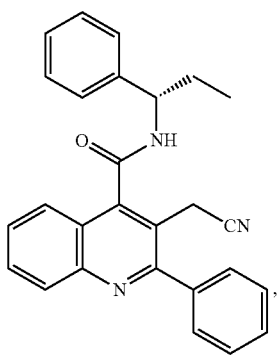
-continued
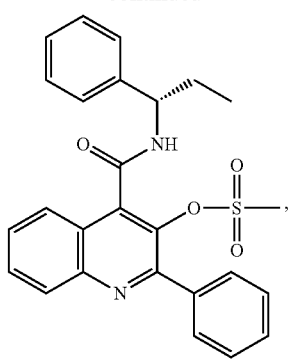
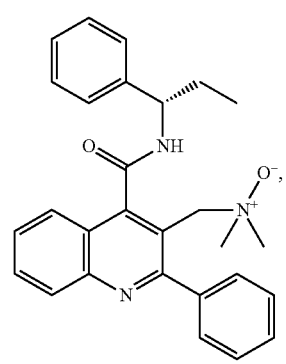
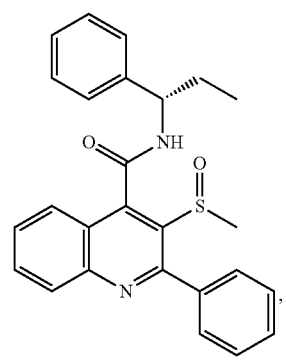
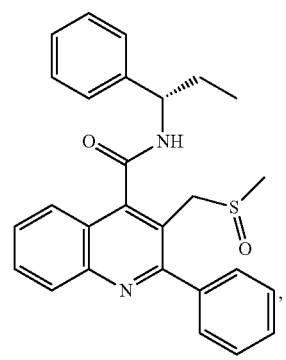

31
-continued
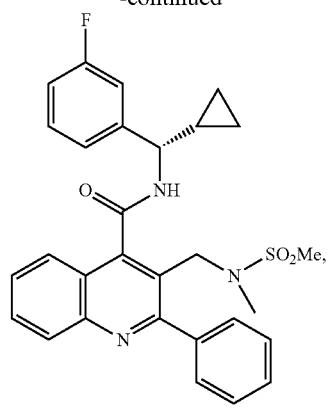
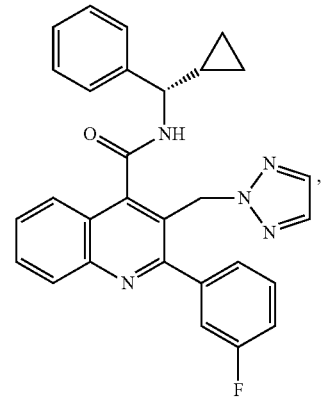
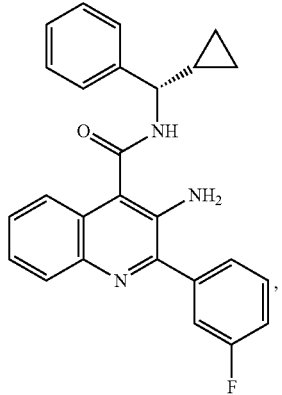
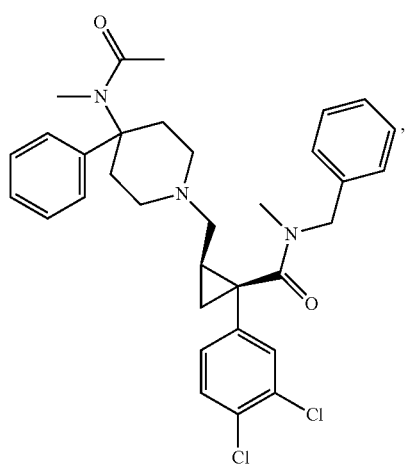
32
-continued
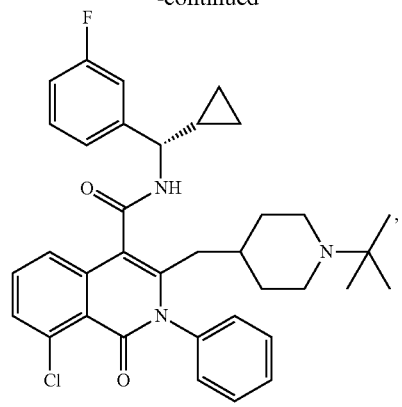
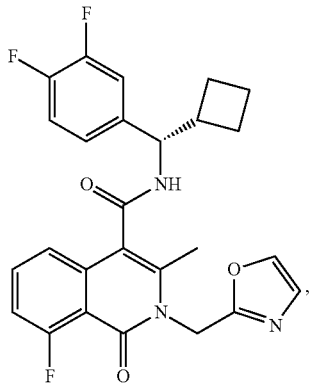
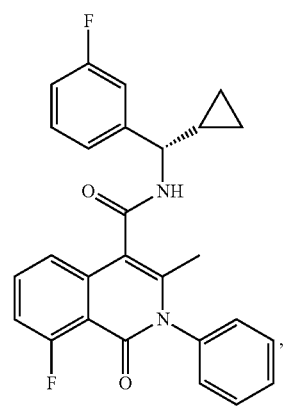
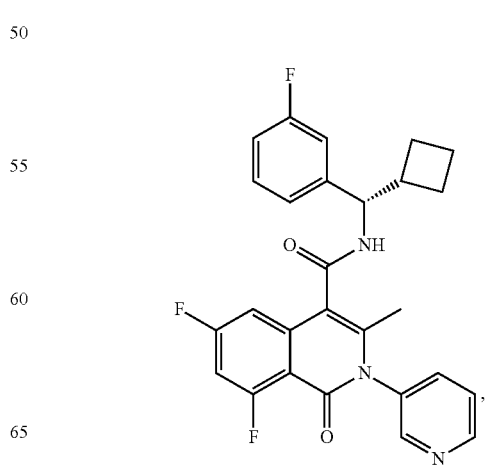

33
-continued
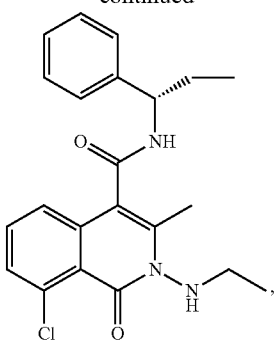
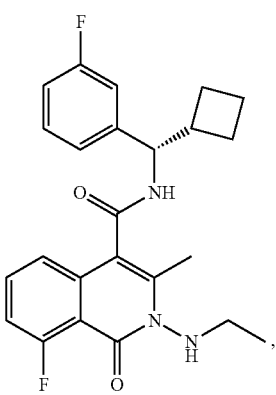
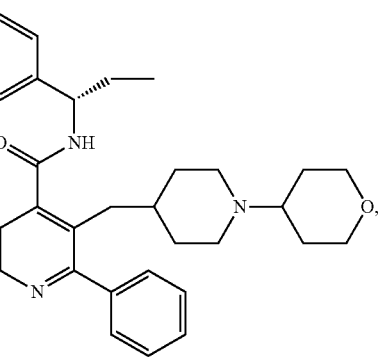
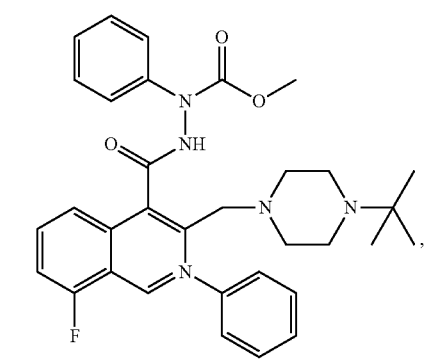
34
-continued
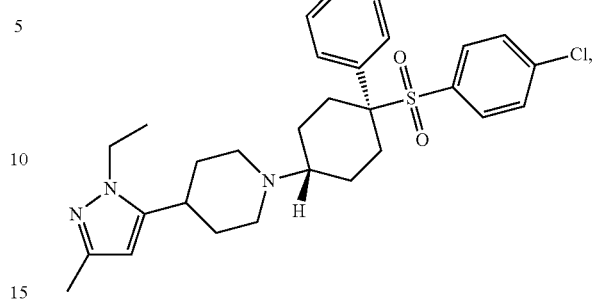
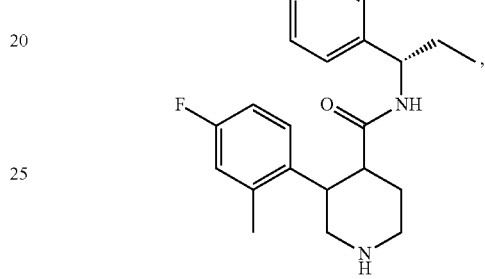
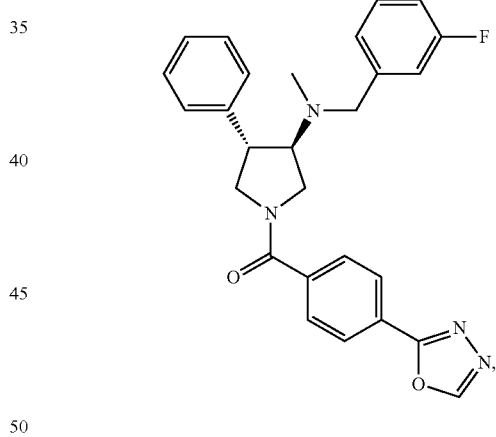
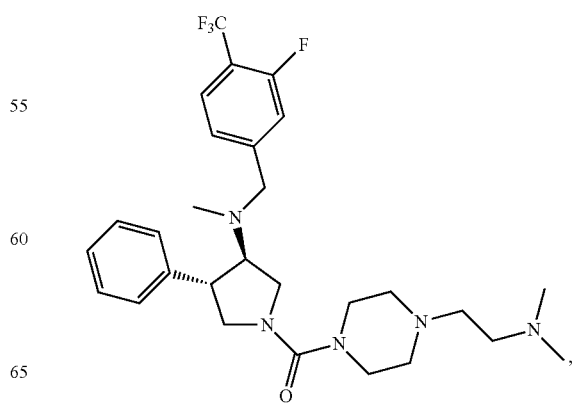

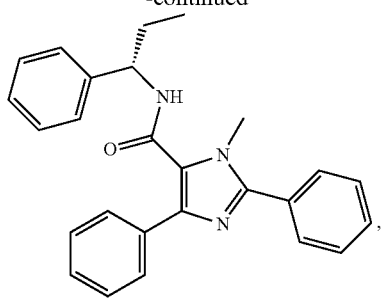
,
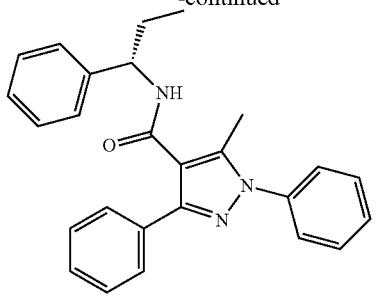
and
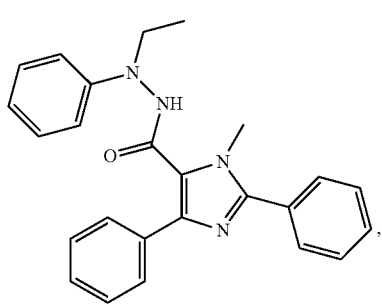
,
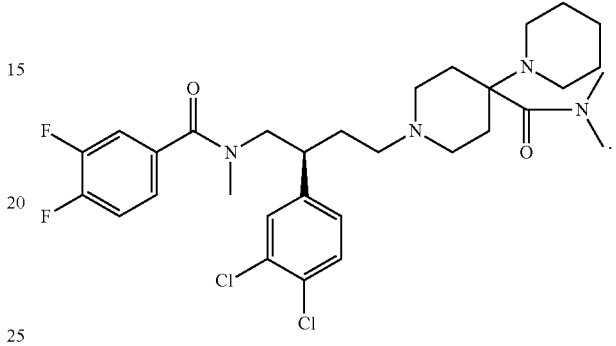
.
* * * * *

Disclaimer

10,052,317 B2 - Waljit Dhillo, Greater London (GB); Channa Jayasena, Greater London (GB). METHOD FOR TREATING OR PREVENTING HOT FLUSHES. Patent dated August 21, 2018. Disclaimer filed December 28, 2020, by the assignee, Imperial College Innovations Limited.

Hereby enters this disclaimer to the complete claims 1, 3-10 and 12 of said patent.

*(Official Gazette, May 25, 2021)*